United States Patent [19]

Ammann et al.

[11] Patent Number: 5,422,340
[45] Date of Patent: Jun. 6, 1995

[54] TGF-β FORMULATION FOR INDUCING BONE GROWTH

[76] Inventors: Arthur J. Ammann; Steven L. Beck; Tue H. Nguyen; Boonsri Ongpipattanakul; Christopher G. Rudman, all of 460 Point San Bruno Blvd., South San Francisco, Calif. 94080-4990

[21] Appl. No.: 255,844

[22] Filed: Jun. 8, 1994

Related U.S. Application Data

[60] Continuation of Ser. No. 3,365, Jan. 12, 1993, Pat. No. 4,733,364, which is a continuation-in-part of Ser. No. 790,856, Nov. 11, 1991, abandoned, which is a division of Ser. No. 401,906, Sep. 1, 1989, Pat. No. 5,158,934.

[51] Int. Cl.$^6$ .................. A61K 38/27; A61K 38/08; A61K 38/22
[52] U.S. Cl. ........................... 514/12; 514/21
[58] Field of Search ................... 514/12, 21

[56] References Cited

U.S. PATENT DOCUMENTS

| | | | |
|---|---|---|---|
| 4,278,630 | 1/1979 | Scheicher | 264/60 |
| 4,702,734 | 10/1987 | Terranova et al. | 514/21 |
| 4,863,732 | 9/1989 | Nathan et al. | 514/21 |
| 4,863,902 | 9/1989 | Amagase | 514/2 |
| 5,158,934 | 10/1992 | Ammann | 514/12 |

FOREIGN PATENT DOCUMENTS

| | | |
|---|---|---|
| 0105014 | 4/1984 | European Pat. Off. |
| 0169016 | 1/1986 | European Pat. Off. |
| 0193372 | 9/1986 | European Pat. Off. |
| 0193917 | 9/1986 | European Pat. Off. |
| 0200341 | 12/1986 | European Pat. Off. |
| 0213776 | 3/1987 | European Pat. Off. |
| 0243179 | 10/1987 | European Pat. Off. |
| 0261599 | 3/1988 | European Pat. Off. |
| 267015 | 5/1988 | European Pat. Off. |
| 0267463 | 5/1988 | European Pat. Off. |
| 0268561 | 5/1988 | European Pat. Off. |
| 0269408 | 6/1988 | European Pat. Off. |
| 0308238 | 3/1989 | European Pat. Off. |
| 0312208 | 4/1989 | European Pat. Off. |
| 0326151 | 8/1989 | European Pat. Off. |
| 0335554 | 10/1989 | European Pat. Off. |
| 0361896 | 4/1990 | European Pat. Off. |
| 0375127 | 6/1990 | European Pat. Off. |
| 0393707 | 10/1990 | European Pat. Off. |
| 0395187 | 10/1990 | European Pat. Off. |
| 0451390 | 10/1991 | European Pat. Off. |
| 0520237 | 12/1992 | European Pat. Off. |
| 0530804 | 3/1993 | European Pat. Off. |
| 2667789 | 4/1992 | France |
| 1153647 | 6/1989 | Japan |
| 2160528 | 12/1985 | United Kingdom |
| WO9001955 | 3/1990 | WIPO |
| WO9004974 | 5/1990 | WIPO |
| WO9005755 | 5/1990 | WIPO |
| WO9009798 | 9/1990 | WIPO |
| WO9014359 | 11/1990 | WIPO |
| WO9103491 | 3/1991 | WIPO |
| WO9119510 | 12/1991 | WIPO |
| WO92/14481 | 9/1992 | WIPO |
| WO9214481 | 9/1992 | WIPO |
| WO93/05823 | 4/1993 | WIPO |

OTHER PUBLICATIONS

Antosz et al., "Transforming Growth Factor-Beta (TGF-β) Inhibits Osteoblastic Differentiation and Bone Formation In Vitro", *J. Dent. Res.*, 67(983):235 (1988).
Bentz et al., "Cartilage Induction and Differentiation: The Role of Bond Derived Cartilage Inducing Factor (CIF-A)", *UCLA Symp. Mol. Cell. Biol.*, 137–147, (1987).

(List continued on next page.)

*Primary Examiner*—Howard E. Schain
*Assistant Examiner*—P. Lynn Touzeau

[57] ABSTRACT

A formulation suitable for inducing bone formation contains about 0.5 μg to about 5 mg of transforming growth factor-β and about 140 mg to about 50 g of tricalcium phosphate and excludes a bone morphogenetic cofactor. In another embodiment, the formulation contains about 0.5 μg to 5 mg transforming growth factor-β, about 140 mg to 50 g of tricalcium phosphate particles, and an amount of amylopectin ranging from about 01:1 to 1:1 amylopectin:tricalcium phosphate.

17 Claims, 10 Drawing Sheets

OTHER PUBLICATIONS

Burger et al., "TGF-B₁ Inhibits Osteoclast Formation in Embyonic Mouse Long Bone Rudiments", *Calcif. Tiss. Int.*, S 32 (F3).

Centrella et al., "Transforming Growth Factor Beta Regulates Osteoblast Replication and Type I Collagen Synthesis by Independent Means", *J. Cell Biol.*, 103:444a(1656) (1986).

Chenu et al., "TGF-β is a Potent Inhibitor of Osteoclast-Like Cell Formation Acting At Multiple Stages of Osteoclast Development", *Calcif. Tiss. Int.*, 42:A10 (39) (1988).

Cotugno et al., "Transforming Growth Factor Beta (TGF-.β) is a Chemoattractant for Periodontal Ligament Cells", *J. Dental Res.*, 67:185(581) (Mar. 1988).

D'Souza et al., *J. Bone & Mineral Res.* 1(1):74 (1986).

Harrod et al., "Effect of Transforming Growth Factor β on Osteoblast-like cells", *Calcif. Tiss. Int.*, 38:S16(62) (1985).

Hock et al., "Transforming Growth factor Beta (TGF-Beta-1) Stimulates Bone Matrix Apposition and Bone Cell Repliation in culture Rat Calvaria", *Calcf Tiss. Int.* 42:A32(124) (1988).

Hollinger et al., "Influence of Exogenous Growth Factors on Osteogenin induced Bone Formation", *J. Den. Res.*, 68:258 (1989).

Ibbotson et al. "Transforming Growth Factors and Bone", *UCLA Symp. Mol. Cell. Biol.*, 349-363 (1987).

Ibbotson et al., *J. Cell Biochem Suppl.*, 10B:108(1986).

Jennings et al., "Comparison of the Biological Actions of TGF Beta-1 and TGF Beta-2: Differential Activity in Endothelial Cells", *J. Cell. Phys.*, 137:167-172 (1988).

Mundy, "The Role of the Bone-Derived Factor TGF β in Bone Coupling", *J. Dent. Res.*, 67:108(S47), (1988).

Pfeilschifter et al., "Transforming Growth Factor Beta (TGF-B) Inhibits Bone Resorption in Fetal Rat Long Bones", *Calcif. Tiss. Int.*, A34:133.

Roberts et al., "Transforming Growth Factor β: Biochemistry and Roles in Embryyogenesis, Tissue Repair and Remodeling and Carcinogenesis", *Recent Progress in Hormone Research*, 44:157-197, (1988).

Robey, "The Effect of Transforming Factor-Beta on Human Bone Cells In Vitro", *Calcif. Tiss. Int.*, A34(135).

Rosen, "TGF-β and Bone Induction", *NY Acad. Sci.*, May 18-20, 1989.

Russell, "The Cellular Control of Bone Formation and Resorption", *J. of Dent. Resear.*, 66:99(S38), (1987).

Seyedin et al. "Cartilage Induction and Differentiation: The Role of Bone Derived Cartilage Inducing Factor (CIF)", *J. Cell Biochem. Suppl.*, 10B:105 (1986).

Sodek et al., "TGF-Beta Effects on Connective Tissue Cells: A Role for TFG-Beta in Wound Healing and Bone Remodeling", *J. Dent. Res.*, 66:191(676) (1987).

Stashenko et al., "Opposing Regulatory Effects of IL-1Beta and Bone Growth Factors on Bone Formation", *J. Dent. Res.*, 68: 192 (1989).

Terek et al, "Transforming Growth Factor-Beta Suppresses Cartilage Specific Gene Expression in Endochondral Bone Repair", *Clinical Research*, 37(2):462A (1989).

Terranova et al., "Biochemically mediated periodontal regeneration", *J. Peridont. Res.*, 22:248-251 (1987).

Valentin-Opran A. et al., "Resorption and formation in metastatic bone", *Rev Rhum Mal Osterartic*, 51(11):pp. 627-632, (1984).

Wakely et al., "Mitogens Produced by Human Bone Cells and Their Potential Role in the Development of a Bone Implant", *Non-Cemented Total Hip Arthroplasty*, 99-109 (1988), ed. Fitzgerald, Jr. (Raven Press, NY 1988).

Beck, LS et al., "Transforming Growth Factor Beta-1 Bound to Tricalcium Phosphate Accelerates Bone Formation Within Skull Defects", *J. Cell Biochem. Suppl. O (17 Part E)*,/p. 25, Mar. 29-Apr. 4, 1993.

Mundy, *Journal of NIH Research*, 1: 65-68 (1989).

Bentz et al, *J. Cell Biol*, 107: 162a (1989).

Sampath et al. *Proc. Natl Acad. Sci USA*, 84:7109-7113 (1988).

Wang et al. *Proc. Natl. Acad. Sci USA*, 85:9484-9488 (1988).

Wozney et al. *Science*, 242:1528-1534 (1988).

Seyedin et al, *J. Biol. Chem.*, 262:1946-1949 (1987).

Seyedin et al. *J. Biol. Chem.*, 261:5693-5695 (1986).

Ibbotson et al. *Science*, 221:1292-1294 (1983).

Hauschka et al., *J. Biol. Chem.*, 261:12665-12674 (1986).

Centrella et al., *FASEB J*, 2:3066-3073 (1988).

Heine, et al., *J. Cell. Biol.*, 105:2861-2876 (1987).

Sandberg et al., *Development*, 102:461-470 (1988).

Sandberg et al., *Devel. Biol.*, 130:324-334 (1988).

(List continued on next page.)

OTHER PUBLICATIONS

Seyedin et al., *Proc. Natl. Acad. Sci USA*, 82:2267-2271 (1985).
Carrington et al. *J. Cell Biol.*, 107:1969-1975 (1988).
Robey et al., *J. Cell Biol.*, 105:457-463 (1987).
Centrella et al. *J. Biol. Chem.*, 262:2869-2874 (1987).
Noda et al., *J. Biol. Chem.*, 263:13916-13921 (1988),
Wrang et al. *J. Cell Biol.*, 106: 915-924 (1988).
Noda & Rodan, J. Cell. Physiol., 133:426-437 (1987).
Pfeilschifter et al., Endocrinology, 121:212-218 (1987).
Centrella et al, Endocrinology, 119:2306-2312 (1986).
Noda & Rodan, Biochem. Biophys. Res. Comm., 140:56-65 (1988).
Noda Endocrinology 124:612-617 (1989).
Tashjian et al. Proc. Natl. Acad. Sci. USA, 82:4535-4538 (1985).
Pfeilschifter et al, J. Clin. Invest., 82:680-685 (1988).
Petkovich et al. J. Biol. Chem, 262:13424-13428 (1987).
Pfeilschifter & Mundy, Proc. Natl. Acad. Sci. USA, 84:2024-2028 (1987).
Chenu et al, Proc. Natl. Acad. Sci. USA, 85:5683-5687 (1988).
Oreffo, et al., Calcified Tissue Internatl. 42:Suppl A15 (1988).
Ignotz & Massague, J. Biol. Chem., 261:4337-4345 (1986).
Bolander et al, New York Academy of Sciences, "Transforming Growth Factor by Chemistry, Biology and Therapeutics", May 18-20, 198 .
Noda et al, J. Cell Biol., 107:48a (1988) (6 Part 3).
Noda & Camilliere, Endocrinology, 124:2991-2994 (1989).
Ibbotson et al, Proc. Natl. Acad. Sci USA, 83:2228-2232 (1986).
Ammann et al., NY Acad. Sci Meeting (May 18, 1989).
Joyce et al., ASBMR/ICCRH Joint Meeting, 1989.
Roberts et al. J. Cell Biol., 103 (5, Part 2) 624a (1986) abs. 34.
Wolf et al., Acta Endocrin. Suppl., 120:(1) 242 (1989).
Pfeilschifter et al, Acta Endocrin. Suppl., 120:(1) 144-145 (1980).
Simpson, Trends Biochem Sci. 9:527-530 (1984).
Sporn et al, Science, 219:1329-1331 (1983).
Keski-Oja et al, J. Cell Biochem, 33(2): 95-107 (1987).
Linkhost et al, Bone 7:479-487 (1986).
Centrella et al., J. Cell Biol, 101:245a (1930) (1985).
Rosen et al., J. Cell Biol., 103:446a (1661) (1986).
Kawamura & Urist, Dev. Biol., 130:435-442 (1988).
Ebford et al., Bone, 8:259-262 (1987).
Komm et al., Science, 241:81-84 (1988).
Globus et al., Endocrin., 123(1):98-105 (1988).
Unedo et al., J. Bone & Min. Res., 4(2):165-171 (1989).
Ibbotson et al., J. Bone & Min. Res., 4(1):37-45 (1989).
Hiraki et al., Biochim & Biophys. Acta, 969:91-99 (1988).
Conatis et al., Calcif. Tiss. Int., 43:346-351 (1988).
Guenther et al., J. Bone & Min. Res. 3(3):269-278 (1988).
Rosen et al, J. Cell. Physiol., 134:337-346 (1988).
Rodon et al., Calcif. Tiss. Int., 41:14 (OPIO) (1987).
Pfeilschifter & Mundy, Calcium Regulation & Bone Metabolism: Basic & Clinical Aspects, Cohn et al., eds., 450-454 (1986).
Hayward & Fiedler-Nagy, Agents & Actions, 22(314):251-254 (19 ).
Sporn et al., J. Cell Biol., 105:1039-1045 (1987).
Roberts & Sporn, Peptide Growth Factors and Their Receptors I, Handbook of Exp. Pharmacology, V. 91/1, Sporn & Roberts, eds., Springer-Verlag, (1990) Chapter 8.
Sporn & Roberts, Nature 332:217-219 (1988).
Terranova & Wikesjo, J. Periodontol., 58(6):371-380 (1987).
Terranova et al., J. Peridontol., 58(4):247-257 (1987).
Terranova et al., J. Periodontol. Res., 21:330-337 (1986).
Terranova & Lyall, J. Periodontol. 57:311-317 (1986).
Stedman's Medical Dictionary, 24th ed., Williams & Wilkins, LA 1984, p. 1058.
Schultz et al., Science, 235:350-352 (1987).
Edwards et al, EMBO J., 6(7):1899-1904 (1987).
Bauer et al., PNAS USA, 82:4132-4136 (1985).
Brown et al., N. Eng. J. Med., 321(2):76-79 (1989).
Roberts et al., FASEB 42:2621-2626 (1983).
Roberts et al., PNAS USA, 78(9):5339-5343 (1981).
Roberts et al., PNAS USA, 82:119-123 (1985).
Chua et al., J. Biol. Chem., 260(9):5213-5216 (1985).
Assoian et al., J. Biol. Chem., 258(11):7155-7160 (1983).
Cheifetz et al., Cell; 48:409-415 (1987).
Centrella et al., J. Bone & Int. Surg., 73-A (9):1418-1428 (1991).
Strassmann et al., Clin. Exp. Immunol., 86:532-536 (1991).

(List continued on next page.)

OTHER PUBLICATIONS

Langer & Moses, J. Cell. Biochem., 45:340–345 (1991).
Beck et al., J. Bone & Min. Res., 6(9):961–968 (1991).
Beck et al., J.Bone & Min. Res., 6(11):1257–1265 (1991).
Jakowlew et al., Mol. Endocr., 2(8):747–755 (1988).
Dijke et al., PNAS USA, 85:4715–4719 (1988).
Derynck et al., J. Biol. Chem., 261(10):4377–4379 (1986).
Sharples et al., DNA, 6(3):239–244 (1987).
Derynck & Rhee, Nucl. Acids Res., 15(7):3187–3189 (1987).
Hanks et al., PNAS USA, 85:79–82 (1988).
Madisen et al., DNA, 7(1):1–8 (1988).
Derynck et al., EMBO J., 7(12):3737–3743 (1988).
Roberts & Sporn, in Peptide Growth Factors & Their Receptors I, 95:3–15 (1990).
Varga & Jimenez, BBRC, 138(2):974–980 (1986).
Masui et al., PNAS USA, 83:2438–2442 (1986).
Shipley et al., Cancer Res., 46:2068–2071 (1986).
Heimark et al., Science, 233:1078–1080 (1986).
Howes et al., Calcif. Tissue Int., 42:34–38 (1988).
Marcelli et al., J. Bone & Min. Res., 5(10):1087–1096 (1990).
Beck et al., Growth Factors, 3:267–275 (1990).
Mackie & Trechsel, Bone, 11:295–300 (1990).
Joyce et al., J. Cell Biol., 110:2195–2207 (1990).

TGF-β FORMULATION FOR INDUCING BONE GROWTH

This is a continuation of U.S. Ser. No. 08/003,365, filed Jan. 12, 1993, now U.S. Pat. No. 4,733,364, which is a continuation-in-part application of U.S. Ser. No. 07/790,856, filed Nov. 11, 1991, now abandoned, which is a divisional application of U.S. Ser. No. 07/401,906, filed Sep. 1, 1989, now U.S. Pat. No. 5,158,934 issued Oct. 27, 1992.

BACKGROUND OF THE INVENTION

1. Field of the Invention

This invention relates to the use of transforming growth factor-beta (TGF-β) to induce bone growth in vivo and to formulations of TGF-β and tricalcium phosphate useful for this purpose.

2. Description of Related Art

The disorders associated with bone loss present major public health problems for Western societies. Osteoporosis alone may affect 20 million Americans in the early years of the next century. Hence, there is wide interest in identifying factors or potential therapeutic agents that inhibit bone loss and stimulate the formation of healthy new bone.

Bone is an extremely complex, but highly organized, connective tissue that is continuously remodeled during the life of an adult by cellular events that initially break it down (osteoclastic resorption) and then rebuild it (osteoblastic formation). This remodeling process occurs in discrete packets throughout the skeleton, i.e., in both cortical bone and trabecular bone. It has recently been reported that mouse bone marrow cells can be stimulated to generate osteoclasts in the presence of parathyroid hormone-related protein or vitamin D. See Akatsu et al., *Endocrinology*, 125: 20–27 (1989); Takahashi et al., *Endocrinology*, 123: 2600–2602 (1988) and Takahashi et al., *Endocrinology*, 123: 1504–1510 (1988).

The currently available therapeutic agents known to stimulate bone formation are fluoride, estrogen, and vitamin D. Fluoride clearly increases trabecular bone mass, but questions remain about the quality of the new bone formed, the side effects observed in some patients, whether there are beneficial effects on vertebral fracture rates, and whether increased fragility of cortical bone with subsequent propensity to hip fracture follows.

Another approach is using agents that promote resorption (parathyroid hormone) and then interrupt resorption (calcitonin). One proposed, but not validated, such sequential therapeutic regimen is coherence therapy, where bone metabolic units are activated by oral phosphate administration and then resorption is inhibited by either diphosphonates or calcitonin.

Within the past few years several factors that stimulate osteoblasts were identified in bone, including TGF-β, fibroblast growth factor, platelet-derived growth factor, insulin-like growth factor I, and β2 macroglobulin. Of these, TGF-β and IGF-I were deemed attractive candidates for factors linking previous bone resorption with subsequent bone formation. Mundy, *The Journal of NIH Research*, 1: 65–68 (1989).

Other proteins stored in the bone matrix may also be important for bone formation. When demineralized bone was injected into the muscle or subcutaneous tissue of rats, a cascade of events, including chondrogenesis, ensued. Urist, *Science*, 150: 893 (1965). This observed activity was due to bone morphogenetic protein (BMP). Since the 1960s several investigators have attempted to identify and characterize this activity. Thus, a protein of 22 Kd, called osteogenin, was identified that possessed the activity. Sampath et al., *Proc. Natl. Acad. Sci. USA*, 84: 7109 (1987). Three proteins from demineralized ovine bone matrix were identified as having this activity. Wang et al., *Proc. Natl. Acad. Sci.*, 85: 9484 (1988) and Wozney et al., *Science*, 242: 1528 (1988). These proteins were named BMP-1, BMP-2A, and BMP-3, the latter two of which belong to the extended TGF-β family by limited sequence homology. These workers modified the assay for bone induction to show cartilage formation but did not show that the proteins ultimately stimulate formation of bone.

The TGF-β group of molecules are each dimers containing two identical polypeptide chains linked by disulfide bonds. The molecular mass of these dimers is about 25 Kd. Biologically active TGF-β has been defined as a molecule capable of inducing anchorage independent growth of target cell lines or rat fibroblasts in in vitro cell culture, when added together with EGF or TGF-α as a co-factor. TGF-β is secreted by virtually all cell types in an inactive form. This latent form can be activated by proteolytic cleavage of mature TGF-β from its precursor (at the Arg-Ala bond in position 278). A non-covalent complex is formed from the association of the mature TGF-β with the precursor remainder or with a protein binding to TGF-β or with alpha$_2$-macroglobulin. This complex is disrupted so as to activate the TGF-β either by exposure to transient acidification or by the action of exogenous proteases such as plasmin or plasminogen activator.

There are at least five forms of TGF-β currently identified, TGF-β1, TGF-β2, TGF-β3, TGF-β4, and TGF-β5. Suitable methods are known for purifying this family of TGF-βs from various species such as human, mouse, monkey, pig, bovine, chick, and frog, and from various body sources such as bone, platelets, or placenta, for producing it in recombinant cell culture, and for determining its activity. See, for example, Derynck et al., *Nature*, 316: 701–705 (1985); European Pat. Pub. Nos. 200,341 published Dec. 10, 1986, 169,016 published Jan. 22, 1986, 268,561 published May 25, 1988, and 267,463 published May 18, 1988; U.S. Pat. No. 4,774,322; Seyedin et al, *J. Biol. Chem.*, 262: 1946–1949 (1987); Cheifetz et al, *Cell*, 48: 409–415 (1987); Jakowlew et al., *Molecular Endocrin.*, 2: 747–755 (1988); Dijke et al., *Proc. Natl. Acad. Sci. (U.S.A.)*, 85: 4715–4719 (1988); Derynck et al., *J. Biol. Chem.*, 261: 4377–4379 (1986); Sharples et al., *DNA*, 6: 239–244 (1987); Derynck et al., *Nucl. Acids. Res.*, 15: 3188–3189 (1987); Derynck et al., *Nucl. Acids, Res.*, 15: 3187 (1987); Derynck et al., *EMBO J.*, 7: 3737–3743 (1988)); Seyedin et al., *J. Biol. Chem.*, 261: 5693–5695 (1986); Madisen et al., *DNA*, 7: 1–8 (1988); and Hanks et al., *Proc. Natl. Acad. Sci. (U.S.A.)*, 85: 79–82 (1988), the entire contents of these publications being expressly incorporated by reference.

TGF-β3, TGF-β4, and TGF-β5, which are the most recently discovered forms of TGF-β, were identified by screening cDNA libraries. None of these three putative proteins has been isolated from natural sources, although Northern blots demonstrate expression of the corresponding mRNAs. TGF-β4 and TGF-β5 were cloned from a chicken chondrocyte cDNA library (Jakowlew et al., *Molec. Endocrinol.*, 2: 1186–1195 [1988]) and from a frog oocyte cDNA library, respectively.

The frog oocyte cDNA library can be screened using a probe derived from one or more sequences of another type of TGF-β. TGF-β4 mRNA is detectable in chick embryo chondrocytes, but is far less abundant than TGF-β3 mRNA in developing embryos or in chick embryo fibroblasts. TGF-β5 mRNA is expressed in frog embryos beyond the neurula state and in Xenopus tadpole (XTC) cells.

TGF-β has been shown to have numerous regulatory actions on a wide variety of both normal and neoplastic cells. TGF-β is multifunctional, as it can either stimulate or inhibit cell proliferation, differentiation, and other critical processes in cell function (M. Sporn, *Science*, 233: 532 [1986]). For a general review of TGF-β and its actions, see Sporn et al., *J. Cell Biol.*, 105: 1039–1045 (1987>, Sporn and Roberts, *Nature.*, 332: 217–219 (1988), and Sporn and Roberts, in Sporn and Roberts, ed., *Handbook of Experimental Pharmacology: Peptide Growth Factors and Their Receptors I*, Springer-Verlag, New York, pp. 3–15 (1990).

The multifunctional activity of TGF-β is modulated by the influence of other growth factors present together with the TGF-β. TGF-β can function as either an inhibitor or an enhancer of anchorage-independent growth, depending on the particular set of growth factors, e.g., EGF or TGF-α, operant in the cell together with TGF-β (Roberts et al., *Proc. Natl. Acad. Sci. U.S.A.*, 82: 119 [1985]). TGF-β also can act in concert with EGF to cause proliferation and piling up of normal (but not rheumatoid) synovial cells (Brinkerhoff et al., *Arthritis and Rheumatism*, 26: 1370 [1983]).

Although TGF-β has been purified from several tissues and cell types, as indicated above, it is especially abundant in bones (Hauschka et al., *J. Biol. Chem.*, 261: 12665 [1986]) and platelets (Assoian et al., *J. Biol. Chem.*, 258: 7155 [1983]). TGF-β is postulated to be one of the local mediators of bone generation and resorption, because of its presence in large amounts in bone and cartilage, because cells with osteoblast and chondrocyte lineage increase replication after exposure to TGF-β, and because TGF-β regulates differentiation of skeletal precursor cells. See Centrella et al., *Fed. Proc. J.*, 2: 3066–3073 (1988).

Immunohistochemical studies have shown that TGF-β is involved in the formation of the axial skeleton of the mouse embryo. TGF-β is also present in other embryos in the cytoplasm of osteoblasts in centers of endochondral ossification and in areas of intramembranous ossification of flat bones, such as the calvarium. Heine et al., *J. Cell. Biol.*, 105: 2861–2876 (1987). Following in situ hybridization of TGF-β1 probes, localization of TGF-β in both osteoclasts and osteoblasts has been described in development of human long bones and calvarial bones. Sandberg et al., *Development*, 102: 461–470 (1988); Sandberg et al., *Devel. Biol.*, 130: 324–334 (1988). TGF-β is found in adult bone matrix (Seyedin et al., *Proc. Natl. Acad. Sci. USA*, 82: 2267–2271 [1985], Seyedin et al., *J. BIOL, Chem.*, 261: 5693–5695 [1986]) and appears at the time of endochondral ossification in an in vivo model of bone formation (Carrington et al., *J. Cell. Biol.*, 107: 1969–1975 [1988]). Cultured fetal bovine bone osteoblasts as well as rat osteosarcoma cells have high mRNA levels for TGF-β and secrete relatively high concentrations of TGF-β (Robey et al., *J. Cell. Biol.*, 105: 457–463 [1987]).

In certain in vitro models, TGF-β was found to stimulate the synthesis of collagen, osteopontin, osteonectin, and alkaline phosphatase, and to stimulate replication in osteoblast-like cells. See Centrella et al., *J. Biol. Chem.*, 262: 2869–2874 (1987); Noda et al., *J. Biol. Chem.*, 263: 13916 (1988); Wrana et al., *J. Cell. Biol.*, 106: 915 (1988); Noda et al., *J. Cell. Physiol.*, 133: 426 (1987); Pfeilshifter et al., *Endocrinology*, 121: 212 (1987); Centrella et al., *Endocrinology*, 119: 2306 (1986); Roby et al., *J. Cell. Biol.*, 105: 457 (1987). In other in vitro models, TGF-β was found to inhibit proliferation and expression of alkaline phosphatase and osteocalcin. See, for example, Noda and Rodan, *Biochem. Biophys. Res. Commun.*, 140: 56 (1986); Noda, *Endocrinology*, 124: 612 (1989).

Further, while Centrella et al., supra, showed increased collagen synthesis after treatment of osteoblasts from rat calvaria with TGF-β, Robey et al., supra, could not show increased synthesis of collagen in fetal bovine bone osteoblasts, postulating that the increased collagen production is secondary to the effects of TGF-β on the proliferation of osteoblasts. In organ culture, TGF-β was reported to stimulate bone resorption in neonatal mouse calvarias, but inhibit resorption in the fetal rat long bone system. See Tashjian et al., *Proc. Natl. Acad. Sci. USA*, 82: 4535 (1981); Pfeilshifter et al., *J. Clin. Invest.*, 82: 680 (1988). TGF-β activity was reported to be increased in cultures of fetal rat calvaria and in calvarial cells incubated with stimulators of bone resorption, such as parathyroid hormone, 1,25-dihydroxyvitamin $D_3$, and IL-1 (Petkovich et al., *J. Biol. Chem.*, 262: 13424–13428 [1987], Pfeilschifter and Mundy, *Proc. Natl. Acad. Sci. USA*, 84: 2024–2028 [1987]). Furthermore, it was reported that TGF-β inhibits the formation of osteoclasts in bone marrow cultures. Chenu et al., *Proc. Natl. Acad. Sci. USA*, 85: 5683–5687 (1988). The showing that TGF-β has effects on both osteoclasts and osteoblasts led Pfeilschifter and Mundy, supra, to propose that it is involved in the strict coupling of the processes of bone resorption and bone formation characteristic of the remodeling process in adult bone. It has also been postulated that the local acidic, proteolytic environment provided by the osteoclasts results in activation of matrix-associated latent TGF-β. Oreffo et al., *Calcified Tiss. Internatl.*, 42: Supp-l:A15 (1988).

In view of the conflicting results reported for in vitro activities, it is not clear whether in vitro models can be used to predict the effects of TGF-β on bone formation and resorption in vivo. See Roberts et al., *Proc. Natl. Acad. Sci. USA*, 82: 119 (1985).

Additional references reporting that TGF-β promotes the proliferation of connective and soft tissue for wound healing applications include U.S. Pat. No. 4,810,691 issued Mar. 7, 1989, U.S. Pat. No. 4,774,228 issued Sep. 27, 1988, Ignotz et al., *J. Biol. Chem.*, 261: 4337 (1986); Varga et al., *Biochem. Biophys. Res. Comm.*, 138: 974 (1986); Roberts et al., *Proc. Natl. Acad. Sci. USA*, 78: 5339 (1981); Roberts et al., *Fed. Proc.*, 42: 2621 (1983); U.S. Pat. No. 4,774,228 to Seyedin et al. TGF-β stimulates the proliferation of epithelia (Matsui et al., *Proc. Natl. Acad. Sci. USA*, 83: 2438 [1986]; Shipley et al. *Cancer Res.*, 46: 2068 [1986]); induces collagen secretion in human fibroblast cultures (Chua et al., *J. Biol. Chem.*, 260: 5213–5216 [1983]); stimulates the release of prostaglandins and mobilization of calcium (Tashjian et al., *Proc. Natl. Acad. Sci. USA*, 82: 4535 [1985]); and inhibits endothelial regeneration (Heimark et al., *Science*, 233: 1078 [1986]).

In wound chambers implanted subcutaneously, TGF-β increased DNA and collagen production. Sporn et al., *Science*, 219: 1329 (1983); Sprugel et al.,

*Am. J. Pathol.*, 129: 601 (1987). Moreover, TGF-β produced collagen fibrosis when injected subcutaneously (Roberts et al., *Proc. Natl Acad. Sci. USA*, 83: 4167–4171 [1986]) and promoted healing of skin incisions in rats (Mustoe et al., *Science*, 237: 1333 [1987]). Nevertheless, although TGF-β induced chondrogenesis in muscle-derived cells in vitro (Seyedin et al., *Proc. Natl. Acad. Sci. USA*, 82: 2267 [1985]; Seyedin et al., *J. Biol. Chem.*, 261: 5693 [1986]), it did not produce cartilage in vivo even when implanted with collagenous substrates, a system used for a long time as a bone induction model in animals (Sampath et al., *Proc. Natl. Acad. Sci. USA*, 84: 7109 [1987]; Howes et al., *Calcif. Tissue Int.*, 42: 34 [1988]).

New studies have shown a time-dependent appearance of mRNA for TGF-β1 at a fracture site in a rat and have localized the peptide immunohistochemically in the periosteum of the healing fracture; the same researchers reported that injections of TGF-β1 into the periosteal area of the femur of young rats have caused significant formation of new cartilage. Bolander et al., *New York Academy of Sciences*, "Transforming Growth Factor-βs: Chemistry, Biology and Therapeutics, May 18–20, 1989. It has been found that injections of TGF-β1 into the parietal bone of young rats stimulated periosteal bone formation, resulting in a thickening of the calvarium. Noda et al., *J. Cell. Biol.*, 107: 48 (1988).

TGF-β was reported to stimulate local periosteal woven bone formation when injected daily onto the periostea of parietal bones of neonatal rats. Noda and Camilliere, *Endocrinology*, 124: 2991–2994 (1989). The fact that TGF-β increases bone thickness when applied adjacent to periosteum in vivo is also reported in Joyce et al., *J. Cell Biol.*, 110: 2195–2207 (1990); Marcelli et al., *J. Bone Min. Rest.*, 5: 1087–1096 (1990); Mackie et al., *Bone*, 11: 295–300 (1990).

Certain researchers reported that TGF-β does not induce bone formation unless it is administered concurrently with a cofactor, e.g., an osteoinductive factor purified from bovine demineralized bone. Bentz et al., supra, U.S. Pat. No. 4,843,063 issued Jun. 27, 1989 to Seyedin et al., and U.S. Pat. No. 4,774,322 issued Sep. 27, 1988.

The remodeling of bone with TGF-β is also described by Centrella et al., *J., Bone and Jt, Surg.*, 73A: 1418–1428 (1991). Multiple applications of TGF-β1 to rat femur induced a profound stimulatory effect with increased deposition of bone at the site of injection. Joyce et al., *J. Bone Min. Res.*, 4: 255–259 (1989). Additionally, a single local application of TGF-β1 in a methylcellulose gel formulation to sites of cartilage damage accelerated the onset and increased the incidence of bone formation adjacent to the cartilage. Beck et al., *J. Bone and Mineral Research*, 6: 961–968 (1991). A single local application of this same formulation in the rabbit skull defect model increased the amount of bone formation in a dose-dependent manner when measured 28 days after injury. Beck et al., *J. Bone Min. Res.*, 6: 1257–1265 (1991).

Phosphate biomaterials have been prepared and investigated in a number of forms. The most widely studied are biodegradable beta tricalcium phosphate (TCP) and hydroxyapatite. A detailed description of the variety of calcium phosphate compositions studied can be found in deGroot, *Bioceramics of Calcium Phosphate*, Boca Raton, Fla., CRC Press, 1983. TCP is used as an in vivo scaffold for bone repair. Perhaps the most consistent and desirable property of TCP as well as other calcium phosphate ceramics is biocompatibility. Also, calcium phosphate ceramics are able to bond directly to bone. Driskell, *Proc. Ann. Conf. Biomed. Eng.*, 15: 199 (1973).

While TCP has low impact resistance, it has application as a bone graft substitute or extender to the extent that proper fixation can be included during the TCP resorption and bone repair processes. It has been demonstrated that TCP in granular form can be used as an autogenous bone extender in the repair of long-bone discontinuities in rabbits. Lemons et al., First World Biomat. Cong. (Baden, Austria), 1980, 4. 10.3 (Abstract). The surgically created defects filled with 50:50 TCP:autogenous bone healed in six weeks as compared with four to six weeks when autogenous bone alone was used. These results indicate that some applications of the granular TCP may be possible in humans where a degree of stress-bearing is a factor. Porous TCP has been applied in block form with some success in mandibular discontinuities in dogs. Tortorelli and Posey, *J. Dent. Res.*, 60: Special Issue A: 601 (1981) (abstract).

The principal clinical application of TCP has been in dentistry. Powdered TCP has been used for initiating apical closure in teeth and for treating periapical defects. Biodegradables may play a role as carriers for bone-inductive agents or bone-cell chemotactic factors. Dipolar microspheres or packets of osteoprogenitor cells donated by an individual may be incorporated within a polymer or ceramic, and in conjunction with characterized bone inductive proteins can be expected to enhance bone repair and augmentation at any chosen skeletal site. Hollinger et al., *Biodegradable Bone Repair Materials*, 207: 290–305 (1986).

TGF-β is typically formulated at an acidic pH at which it is active. Various methods for its formulation include adding 2–5% methylcellulose to form a gel (Beck et al., *Growth Factors*, 3: 267–275 [1990] reporting the effects on wound healing of TGF-β in 3% methylcellulose), adding collagen to form an ointment or suspension (EP 105,014 published 4 Apr. 1984; EP 243,179 published 28 Oct. 1987; EP 213,776 published 11 Mar. 1987), or adding a cosmetically acceptable vehicle to the TGF-β for a topical formulation (U.S. Pat. No. 5,037,643 issued 6 Aug. 1991).

Additionally, human topical applications containing growth factors such as TGF-β are described in EP 261,599 published 30 Mar. 1988. A slow-release composition of a carbohydrate polymer such as a cellulose and a protein such as a growth factor is disclosed in EP 193,917 published 10 Sep. 1986. A formulation of a bioactive protein and a polysaccharide is described in GB Pat. No. 2,160,528 granted 9 Mar. 1988. An intranasally applicable powdery pharmaceutical composition containing an active polypeptide, a quaternary ammonium compound, and a lower alkyl ether of cellulose is described in EP 193,372 published 3 Sep. 1986. See also U.S. Pat. No. 4,609,640 issued 2 Sep. 1986 disclosing a therapeutic agent and a water-soluble chelating agent selected from polysaccharides, celluloses, starches, dextroses, polypeptides, and synthetic polymers able to chelate Ca and Mg; and JP 57/026625 published 12 Feb. 1982 disclosing a preparation of a protein and water-soluble polymer such as soluble cellulose. In addition, a method for entrapping enzymes in gel beads for use as a biocatalyst is described in U.S. Pat. No. 3,859,169. Also, a method for preparing polyvinyl alcohol gel intended as a transdermal vehicle for water-soluble synthetic drugs is disclosed in JP 62/205035 published 9 Sep. 1987.

A purified particulate bone mineral product for use in medicine impregnated with a gel-forming protein or polysaccharide such as gelatin is disclosed that may also carry one or more absorbed drugs such as transforming bone growth factor. WO 90/01955 published 8 Mar. 1990. Use of TGF-$\beta$ and a biocompatible controlled release polymer is described by Langer and Moses, *J. Cell. Biochem.*, 45: 340–345 (1991). An osteoinductive pharmaceutical formulation comprising an antifibrinolytic agent such as epsilon amino acid caproic acid or other lysine analogue or serine protease inhibitor and a cartilage and/or bone inductive protein such as bone morphogenetic protein is disclosed in WO 91/19510 published 26 Dec. 1991. The formulation may additionally contain a growth factor such as TGF-$\beta$ and may be encased in a TCP matrix. Biologically active polypeptides based on TGF-$\beta$ sequences disclosed as useful Ln the treatment of wounds and bone fractures are described in WO 90/14359 published 29 Nov. 1990. In addition, TGF-$\beta$ has been disclosed as a treatment for gingivitis and periodontal disease in the form of implants, microspheres, an absorbable putty-like matrix, or a polymeric material having the drug impregnated thereon. WO 90/04974 published 17 May 1990. Compositions with activin, also optionally containing a TGF-$\beta$, a bone morphogenetic protein, or bone marrow, have been formulated with hydroxyapatite and TCP as a dental and orthopedic implant and for bone growth induction. WO 92/14481 published 3 Sep. 1992. Also, TGF-$\beta$ formulated for treatment of inflammatory disorders is described in EP 269,408 published 1 Jun. 1988. Additionally disclosed are cytokines such as TGF-$\beta$ bound to a solid support, which may include ceramics and polymeric materials as well as insoluble protein materials such as gelatin, collagen, or albumin. WO 90/09798 published 7 Sep. 1990.

Stable lyophilized formulations of polypeptide growth factors such as TGF-$\beta$ containing polymers to impart viscosity to a reconstituted solution or polysaccharides to stabilize against loss of biological activity are described in EP 308,238 published 22 Mar. 1989 and EP 267,015 published 11 May 1988, respectively. See also EP 335,554 published 4 Oct. 1989 on a cosmetic composition suitable for topical application to mammalian skin or hair that can contain collagen, a gelatin, and powders such as starch and aluminum silicates. Gels with polymeric material for providing viscosity that may contain a polypeptide growth factor such as TGF-$\beta$ are described in EP 312,208 published 19 Apr. 1989. Collagen-polymer conjugates in admixture with particulate matter such as TCP are described by WO 90/05755 published 31 May 1990. A controlled drug delivery system for placement in a periodontal pocket containing discrete microparticles comprising the drug (e.g., TGF-$\beta$) and a polymer is described in EP 451,390 published 16 Oct. 1991. A bioactive compound associated with liposomes that may include TGF-$\beta$ is described in EP 393,707 published 24 Oct. 1990 and in Strassman et al., *Clin. Exp. Immunol.*, 86: 532–536 (1991).

A sustained-release formulation containing an active ingredient such as TGF and collagen and a least one organic acidic compound is described in EP 326,151 published 2 Aug. 1989. TGF-$\beta$ in combination with a proteinaceous matrix that may comprise collagen and/or fibrinogen is described by WO 91/03491 published 21 Mar. 1991. A collagen sponge useful as an implant for a wound-healing matrix for TGF-$\beta$ and FGF is described in U.S. Pat. No. 4,950,483 issued 21 Aug. 1990. A therapeutic drug that contains a growth factor may be formulated in the form of powder, granules, etc., for example, with gelatin. JP 1-153647 published 15 Jun. 1989. Cicatrising compositions containing activated TGF-$\beta$ may be formulated with polysaccharides and humectants such as glycerol. FR 2,667,789 published 17 Apr. 1992.

It has also been known to mix an active medicament unstable to heat with a biodegradable protein carrier such as collagen, atelocollagen, or gelatin to form a carrier matrix having sustained-release properties. The resultant mixture is then dried, and the dried material is formed into an appropriate shape, as described in U.S. Pat. No. 4,774,091.

It would be desirable to provide a formulation for TGF-$\beta$ with the proper consistency suitable for molding to fill in bone gaps where needed.

Accordingly, it is an object of the present invention to provide a suitable formulation of exogenous TGF-$\beta$ to a local site on an animal where skeletal (bony) tissue is deficient so as to produce in every case mature, morphologically normal bone at the site of administration where it is needed.

It is another object to provide a bone-inducing composition that is clinically relevant for filling in smaller bone defects than is required for prosthetic devices.

It is further object to provide a TGF-$\beta$ formulation with enhanced consistency for improved application to the desired bone defect site.

These and other objects will become apparent to those skilled in the art.

SUMMARY OF THE INVENTION

The above objects are achieved by providing a bone-inducing formulation comprising an effective amount of TGF-$\beta$ and TCP. The TCP includes TCP ceramics as well as TCP particles. In a specific aspect, this formulation is a bone-inducing formulation comprising about 0.5 $\mu$g to about 5 mg TGF-$\beta$, more preferably 5 $\mu$g to about 3 mg TGF-$\beta$, adsorbed onto about 140 mg to about 50 g TCP particles, preferably granules.

In a preferred aspect, the formulation also contains an effective amount of a polymer for enhancing consistency of the formulation. More preferably, the polymer is amylopectin. In a specific aspect, this bone-inducing formulation comprises about 0.5 $\mu$g to about 5 mg TGF-$\beta$, about 140 mg to about 50 g TCP particles, and an amount of amylopectin that ranges from about 0.1:1 to 1:1 amylopectin:TCP, prefarably about 0.25:1 to 0.5:1 amylopectin:TCP.

In another aspect, the invention provides a method of producing a bone-inducing formulation of TGF-$\beta$ comprising admixing an effective amount of a liquid solution of the TGF-$\beta$ with TCP granules for a sufficient period of time to adsorb the TGF-$\beta$ onto the granules and contacting the resulting mixture with an effective amount of amylopectin.

These aspects of the invention enable preparation of a suitable formulation for the generation of normal mature bone every time only where it is required at a particular site. Preclinical results with TGF-$\beta$ applied topically as described below show new bone formation in various animal models.

DESCRIPTION OF THE PREFERRED EMBODIMENTS

Figure 1:
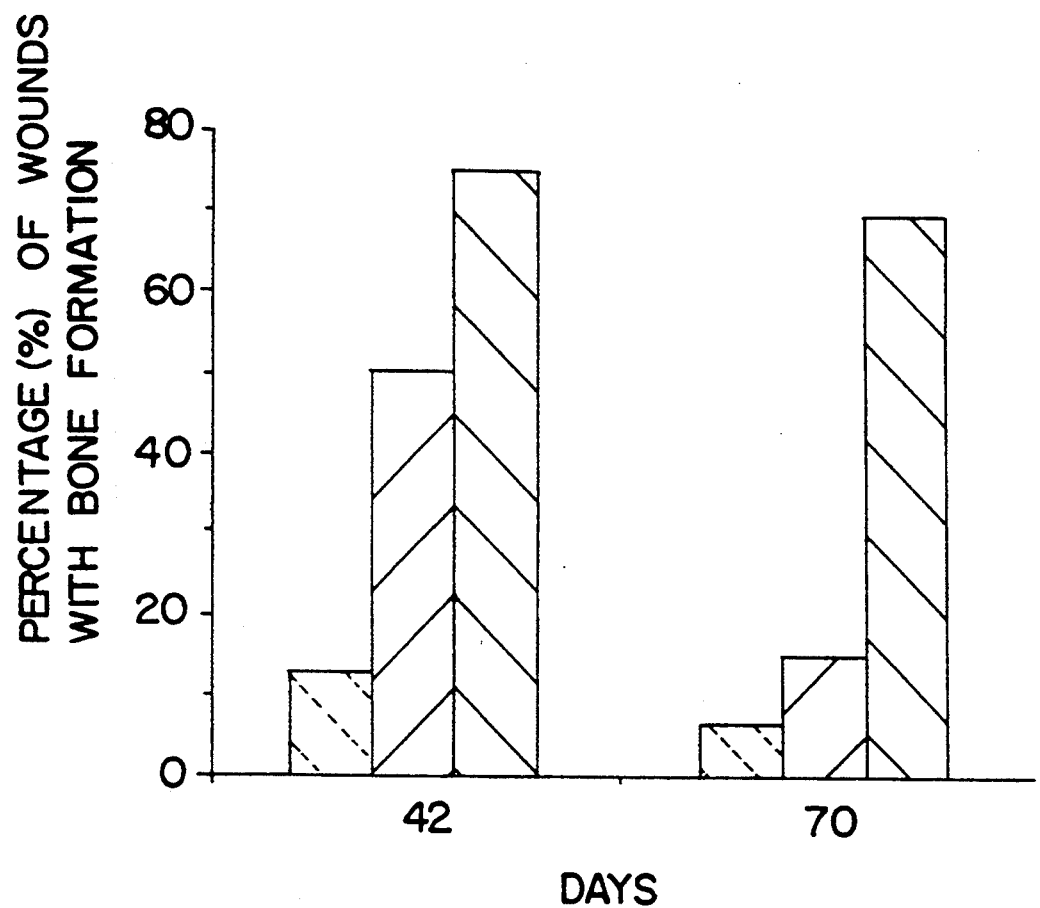
FIG. 1 illustrates the percentage of wounds with bone formation when placebo (left-most bar), recombinant human TGF-1 (rhTGF-$\beta$1) at 25 ng/wound (middle bar), or rhTGF-$\beta$1 at 100 ng/wound (right-most bar) is applied in the rabbit ear ulcer model at 42 and 70 days after wounding. Maximum bone formation was observed at day 42.

A. Definitions:

The "polymer for enhancing consistency of the formulation" may be any polysaccharide or insoluble protein material useful for binding the TGF-$\beta$ to the TCP to form a smooth, moldable putty or paste. Especially preferred are carbohydrates such as agarose, cross-linked agarose, dextran, cross-linked dextran, inulin, hyaluronic acid, cellulose, cellulose derivatives such as carboxymethyl cellulose, starch derivatives such as amylopectin, and insoluble protein materials such as gelatin, including lyophilized gelatin with glycerol, collagen, or albumin, or a combination of any of these.

The collagen may be chemically conjugated to a synthetic hydrophilic polymer and mixed with the TCP as described in WO 90/05755, supra. The preferred polymer herein is amylopectin, most preferably potato amylopectin. Amylopectin is the branched component of starch; it is formed through chains of D-glucopyranose residues linked together mainly by (1→4)-$\alpha$-D linkages but with 5-6% of (1→6)-$\alpha$-D bonds at the branch points. It is further described in *Molecular Biology, an International Series of Monograms and Textbooks*, The Polysaccharides, Vol. 3, Gerald Aspinall, ed. (Academic Press, 1985), pp. 216-223.

"Tricalcium phosphate" or "TCP" has a nominal composition of $Ca_3(PO_4)_2$ and is found in two different whitlockite crystallographic configurations, $\alpha$-TCP, and the more stable, $\beta$-TCP. It is an extremely biocompatible material used for filling bone and dental defects. It is described, for example, by Damien and Parsons, *J. App. Biomaterials*, 2: 187-208 (1991), Ricci, *Biomedical Engineering: Recent Developments*, Saha editor, "Development of a Fast-Setting Ceramics-Based Grout Material for Filling Bone," p. 475-481 (1986), Bowers et al., *J. Periodontal*, 57: 286-287 (1986). It has also been used with bone morphogenetic protein as a delivery system. Urist et al., *Clin. Orthop.*, 187: 277-280 (1984). TCP is commercially available from, for example, DePuy, but also may be synthesized, for example, by the method described in *Biomedical Sciences Instrumentation*, Instrument Society of America, Ed. David Carlson, Vol. 27, Paper #91-026, Benghuzzi et al., p. 197-203 (1991). The preferred TCP herein is $\beta$-TCP, and in the examples below, the term "TCP" refers to $\beta$-TCP.

By "bone inducing" is meant promoting the formation of morphologically normal, mature bone only at a site where there is a bone deficiency that needs to be replaced. Mature bone is bone of any type, whether cortical or trabecular, that is mineralized as opposed to immature or cartilaginous bone as would be formed in a neonatal model. Morphologically normal bone is bone that is detected histologically as normal (i.e., consisting of endochondral or membranous type lamellar bone and including marrow spaces with osteoblasts and osteoclasts). This is in contrast, for example, to callous formation with a fibrotic matrix as seen in the first stage of fracture healing. Thus, the bone induction herein is contemplated not only as acceleration of bone regeneration, as in a fracture, but also as stimulation of the formation of bone that is returned to its normal morphological state.

By "skeletal tissue deficiency" is meant a deficiency in bone at any site where it is desired to restore the bone, no matter how bone deficiency originated, e.g., whether as a result of surgical intervention, removal of tumor, ulceration, implant, or fracture.

By "bone morphogenetic cofactor" is meant a protein originally found in the bone matrix that induces all of the cascade events involved in the osteoinductive process in vivo, including chondrogenesis, vascular invasion, formation of a marrow cavity, and eventually formation of a bone ossicle. Such factors include the bone morphogenetic proteins as found in demineralized bone (Urist, *Science*, 150: 893 [1965]), osteogenin, a 22 Kd protein with this activity (Sampath et al., *Proc. Natl. Acad. Sci. USA*, 84: 7109 [1987]), a glycoprotein called osteoinductive factor (U.S. Pat. No. 4,843,063, supra), and BMP-1, BMP-2A, and BMP-3 from demineralized ovine bone matrix (Wang et al, *Proc. Natl. Acad. Sci. USA*, 85: 9484 [1988]; Wozney et al., *Science*, 242: 1528

[1988]), the disclosures of all of which references are incorporated herein by reference.

The osteoinductive cofactor described in the U.S. patent is isolated from bone, preferably a bovine metatarsal bone, wherein the demineralized bone is prepared, non-collagenous proteins are extracted from the bone, the extract is subjected to gel filtration, the fraction constituting a low molecular weight (10,000–40,000 daltons) possessing the greatest chondrogenic activity is subjected to ion exchange chromatography, the first fraction CM-1 is subjected to RP-HPLC, and two peaks of predominantly 28 Kd and 36 Kd chondrogenic/osteogenic cofactor protein are purified to give single bands on SDS-PAGE. These cofactors and the others mentioned above are included in the term "bone morphogenetic cofactor."

By "osteogenic cell source" is meant a source of viable cells that are capable of forming bone, as well as viable cells that are precursors to cells capable of forming bone, including a source of cells capable of recruiting or stimulating cells capable of forming bone. Suitable such sources include dispersed whole bone marrow cells (obtained by, e.g., aspiration or mechanical agitation), perichondrium, periosteum, or a suitable cell line. For example, the cells may be taken from a site of the animal to be treated adjacent to the deficiency (e.g., periosteum stripped from an adjacent site to the defect such as a fracture site or a surgical excision site) or from a biopsy site of the animal (e.g., one that has been previously accessed, e.g., the hip), or from bone marrow.

By "animal" is meant any animal having a vertebrate structure, preferably a mammal, and most preferably a human.

By "TGF-$\beta$" is meant the family of molecules described hereinabove that have either the full-length, native amino acid sequence of any of the TGF-$\beta$s from any species, including the latent forms and associated or unassociated complex of precursor and mature TGF-$\beta$ ("latent TGF-$\beta$"). Reference to such TGF-$\beta$ herein will be understood to be a reference to any one of the currently identified forms, including TGF-$\beta$1, TGF-$\beta$2, TGF-$\beta$3, TGF-$\beta$4, and TGF-$\beta$5, each of which is represented by certain species indicated in FIG. 1 of U.S. Pat. No. 5,158,934 issued Oct. 27, 1992 and latent versions thereof, as well as to TGF-$\beta$ species identified in the future, including polypeptides derived from the sequence of any known TGF-$\beta$ and being at least 75% homologous with the sequence. Members of the TGF-$\beta$ family are defined as those which have nine cysteine residues in the mature portion of the molecule, share at least 65% homology with other known TGF-$\beta$ sequences in the mature region, and compete for the same receptor. In addition, they all appear to be encoded as a larger precursor that shares a region of high homology near the N-terminus and shows conservation of three cysteine residues in the portion of the precursor that will later be removed by processing. Moreover, the TGF-$\beta$s appear to have a four- or five-amino-acid processing site.

B. Modes for Carrying Out the Invention:

The invention is carried out in one aspect by mixing the TGF-$\beta$ with a suitable pharmaceutical carrier, and without the bone morphogenetic cofactor, and administering the resulting composition locally to a site on an animal where it is desired to induce formation of normal, adult bone and where a source of osteogenic cells and their precursor cells are present at the site. If the site does not naturally have a source of osteogenic cells present, the pharmaceutical composition also contains an osteogenic cell source as defined above, in an amount sufficient to induce bone growth.

Examples of indications where promotion of bone repair at a skeletal site is important include periodontal disease where root socket healing is impaired (tooth socket sites), non-union fractures, including primary treatment of high risk fractures and adjunctive treatment with bone grafting or bone substitutes for established non-union fractures, large bony defects caused by trauma or surgery [e.g., partial mandibular resection for cancer, large cranial defects, spinal (vertebral) fusions, correction of severe scoliosis by surgical alignment held in place with a Harrington bar (to shorten the six months normally required for a body cast), and spinal fractures with open reduction (to decrease significantly the period of immobilization)], and rapid stabilization and enhanced fixation of artificial prostheses and spacer bars, oral joints, and bone replacements.

Examples of the latter include plastic and reconstructive surgery, fixation of permanent dentures into mandible, enhanced fixation of accepted joint prosthesis, e.g., hips, knees, and shoulders (leading to the acceptance of prostheses that until now have been unacceptable due to rapid loosening and instability such as elbows), and limb salvage procedures, usually associated with malignancy (the bone shaft may be removed but the articular surfaces are left in place and connected by a space bar; rapid and enhanced fixation is required for success). If the site constitutes a periodontal site, i.e., one that involves the teeth, gums, and dental sockets, the TGF-$\beta$ is suitably administered in conjunction with an exogenously added source of osteogenic cells.

In one preferred embodiment, the TGF-$\beta$ is administered by treating a device with the TGF-$\beta$ composition and implanting the device into the animal at the site of the deficiency, the composition also containing the osteogenic cell source when the site is deficient in such cells. The device may consist of any device suitable for implantation, including a molded implant, plug, prosthetic device, capsule, titanium alloy, sponge, or ceramic block. Examples of suitable delivery vehicles useful as devices are those disclosed by Nade et al., Clin. Orthop. Rel. Res., 181: 255–263 (1982); Uchida et al., J. Biomed. Mat. Res., 21: 1–10 (1987); Friedenstein et al., Exp. Hematol., 10: 217–227 (1982); Deporter et al., Calcif. Tissue Int., 42: 321–325 (1988); McDavid et al., J. Dent. Res.,. 58: 478–483 (1979); Ohgushi et al., J. Orthopaedic Res., 7: 568–578 (1989); Aprahamian et al., J. Biomed. Mat. Res., 21: 965–977 (1986); Emmanual et al., Stain. Tech., 62: 401–409 (1987), the disclosures of all of which references are incorporated herein by reference.

For bone defects involving gaps, such as a dry socket or non-union fracture, a plug may be used to fill the gap. The plug may be composed of, for example, hydroxyapatite or collagen on which TGF-$\beta$ is adsorbed. For larger bone defects resulting from, e.g., trauma or skeletal reconstruction around an ulcer or hip prosthesis, the device is preferably a made-to-fit ceramic block. More preferably, the ceramic block comprises 0–100% hydroxyapatite and the remaining 100–0% TCP, by weight, most preferably 60% hydroxyapatite and 40% TCP.

In a specific embodiment for a jaw implant, a calcium carbonate moldable material or Interpore ™ molding device is molded to fit the jaw using a 3-dimensional x-ray of the jaw before surgery, and the molded material is impregnated with TGF-$\beta$. Then, dispersed bone marrow from another site of the animal (e.g., from the hip) is infiltrated into the mold, and the mold is placed into the jaw for final implantation.

Preferably, the device is treated with the TGF-$\beta$ composition (which includes both a solution and a gel formulation) for a sufficient period of time to allow adsorption, and to allow drying in the case of the gel. The concentration of TGF-$\beta$ in the solution or gel and the time of exposure depend on a number of factors, including the volume of the defect, the potency of the TGF-$\beta$ polypeptide, and the nature of the site to which it is applied, and will be adjusted accordingly. As the size of the defect increases, or when the site is other than a bone site, the concentration of TGF-$\beta$ and the time of presoaking should be increased. The treatment is for preferably at least about 0.5 hour, depending on the factors mentioned above (more preferably at least about 1 hour, and most preferably 1–2 hours), before implantation. Also depending on the above considerations, the concentration of TGF-$\beta$ in the TGF-$\beta$ composition for treating the device is preferably at least about 1 ng/ml (more preferably at least about 1–10 up to 100 ng/ml). The treatment may consist of any mode by which the composition is applied to the device to deliver effectively the TGF-$\beta$ and the osteogenic cell source. Such treatment includes, for example, adsorption, covalent crosslinking, or impregnation, depending in part on the nature of the indication.

The TGF-$\beta$ compositions to be used in the therapy will be dosed in a fashion consistent with good medical practice taking into account the nature of the skeletal tissue deficiency to be treated, the species of the host, the medical condition of the individual patient, the presence of any other cotreatment drug in the composition, the site of delivery of the agent, the method of administration, the scheduling of administration, and other factors known to practitioners. Because of differences in host response, significant site-to-site and patient-to-patient variability exists. For purposes herein, the "therapeutically effective amount" of TGF-$\beta$ is an amount that is effective to induce bone growth, as defined above, at the site of skeletal tissue deficiency.

As a general proposition, the TGF-$\beta$ is formulated and delivered to the target site at a dosage capable of establishing at the site a TGF-$\beta$ level greater than about 0.1 ng/ml. Typically, the TGF-$\beta$ concentrations range from about 0.1 ng/ml to 5 mg/ml, preferably from about 1 to 2000 ng/ml. These intra-tissue concentrations are maintained preferably by topical application and/or sustained release.

As noted above, these suggested amounts of TGF-$\beta$ are subject to a great deal of therapeutic discretion. The key factor in selecting an appropriate dose and scheduling is the result obtained. Clinical parameters to determine an endpoint include increases in bone formation and mass and increases in radiographically detectable bone. Such measurements are well known to those clinicians and pharmacologists skilled in the art.

The TGF-$\beta$ composition is administered locally to the site by any suitable means, including topical and continuous-release formulation. The active TGF-$\beta$ ingredient is generally combined at ambient temperature at the appropriate pH, and at the desired degree of purity, with a physiologically acceptable carrier, i.e., a carrier that is non-toxic to the patient at the dosages and concentrations employed. The carrier may take a wide variety of forms depending on the form of preparation desired for administration.

To be effective, the TGF-$\beta$ is converted by the body to its activated form, i.e., the mature form is cleaved from its precursor using a suitable enzyme and the resultant complex is treated with acid or other appropriate agent to activate the TGF-$\beta$. Nevertheless, TGF-$\beta$ is suitably administered in an inactive or delayed-release form such as a complex of mature TGF-$\beta$ with proTGF-$\beta$ not containing mature TGF-$\beta$ (i.e., the remaining precursor of TGF-$\beta$), with a TGF-$\beta$ binding protein, or with alpha$_2$-macroglobulin. The latent form is then converted to the active form either by naturally occurring mechanisms in the local environment or by formulation with TGF-$\beta$ activating agents described above. See, e.g., Gentry et al., *Mol. Cell. Biol.*, 8: 4162–4168 (1988); Miyazono et al., *J. Biol. Chem.*, 263: 6407–6415 (1988); Wakefield et al., *J. Biol. Chem.*, 263: 7646–7654 (1988); Keski-Oja et al., *J. Cell Biochem. Suppl.*, 11A: 60 (1987); Kryceve-Martinerie et al., *Int. J. Cancer*, 35: 553–558 (1985); Lawrence et al., *Biochem. Biophys. Res. Commun.*, 133: 1026–1034 (1985); Lawrence et al., *J. Cell physiol.*, 121: 184–188 (1984). Thus, the pH of the TCF-$\beta$ composition may suitably reflect the conditions necessary for activation.

For the preparation of a liquid composition suitable for impregnation of a device, the carrier is suitably a buffer, a low molecular weight (less than about 10 residues) polypeptide, a protein, an amino acid, a carbohydrate including glucose or dextrans, a chelating agent such as EDTA, a cellulose, or other excipient. In addition, the TGF-$\beta$ composition is preferably sterile. Sterility is readily accomplished by sterile filtration through (0.2 micron) membranes. TGF-$\beta$ ordinarily will be stored as an aqueous solution, as it is highly stable to thermal and oxidative denaturation, although lyophilized formulations for reconstitution are acceptable.

Generally, where the bone disorder permits, one should formulate and dose the TGF-$\beta$ for site-specific delivery, where the TGF-$\beta$ is formulated into a sterile composition suitable for local application to the desired site.

For local application of the TGF-$\beta$ composition, for example, in the case of a bone defect that is a crack, e.g., a union fracture, the carrier may be any vehicle effective for this purpose. For obtaining a gel formulation, the liquid composition is typically mixed with an effective amount of a water-soluble polysaccharide, polyethylene glycol, or synthetic polymer such as polyvinylpyrrolidone to form a gel of the proper viscosity to be applied topically. The polysaccharide is generally present in a gel formulation in the range of 1–90% by weight of the gel, more preferably 1–20%. Examples of other suitable polysaccharides for this purpose, and a determination of the solubility of the polysaccharides, are found in EP 267,015, published May 11, 1988, the disclosure of which is incorporated herein by reference.

The polysaccharide that may be used for the gel includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the TGF-$\beta$ held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low- and high-molecular-weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

In a preferred embodiment, the gel contains about 2–5% by weight methylcellulose and the TGF-$\beta$ is present in an amount of about 10–1000 $\mu$g per ml of gel. More preferably, the gel consists of about 3% methylcellulose by weight, lactic acid to pH 5.0, and 20–200 $\mu$g per ml of TGF-$\beta$. This corresponds to a dose of 1–10 $\mu$g of TGF-$\beta$ per 50 $\mu$l of gel.

For the preparation of a sustained-release formulation, the TGF-$\beta$ is suitably incorporated into a biodegradable matrix or microcapsular particle. A suitable material for this purpose is a polylactide, although other polymers of poly ($\alpha$-hydroxycarboxylic acids), such as poly-D-(−)-3-hydroxybutyric acid (EP 133,988), can be used. Additional biodegradable polymers include poly(lactones), poly(acetals), poly(orthoesters) or poly(orthocarbonates). The TGF-$\beta$ is also suitably mixed with a biodegradable protein carrier such as collagen, atelocollagen, for example, one by Koken Co., Ltd., or gelatin to form a carrier matrix having sustained-release properties; the resultant mixture is then dried, and the dried material is formed into an appropriate shape, as described in U.S. Pat. No. 4,774,091. Collagen may be prepared by mincing calf skin and defatting it in chloroform: methanol (1:1), washing with 4% EDTA (pH 7.4), and digesting with pepsin solution (pH 2.2; substrate: enzyme ratio, 100:4) for 72 hours at 15° C. The collagen solubilized with pepsin is purified by differential precipitation at neutral pH and a salting-out procedure (6% NaCl, pH 3.0, 12 hours) described by Kresina and Miller, *Biochemistry*, 18: 3089 (1979). The purified collagen is dissolved in 0.01N HCl (3 mg collagen/ml), sterilized by filtration through a Millipore membrane (pore size 0.45 $\mu$m), and freeze-dried. Then it is redissolved in 0.01N HCl (10 mg collagen/ml) under sterile conditions and kept in a refrigerator until use.

The initial consideration here must be that the carrier itself, or its degradation products, are non-toxic in the target bone site and will not further aggravate the condition. This can be determined by routine screening in animal models of the target bone disorder or, if such models are unavailable, in normal animals. For examples of sustained-release compositions, see U.S. Pat. No. 3,773,919; EP 58,481; U.S. Pat. No. 3,887,699; EP 158,277; Canadian Patent No. 1,176,565; Sidman et al., *Biopolymers*, 22: 547 (1983), and Langer et al., *Chem. Tech.*, 12: 98 (1982).

Controlled delivery of TGF-$\beta$ to a site also is suitably accomplished using permeable hollow cellulose acetate fibers with the TGF-$\beta$ that are placed in the site and removed 24 hours later or left for longer periods of time (U.S. Pat. No. 4,175,326). Also, acrylic resin strips or cast films can be impregnated with TGF-$\beta$ and applied to the affected site. In addition, narrow dialysis tubing can be filled with a TGF-$\beta$ solution and placed so as to deliver TGF-$\beta$ to the appropriate site.

Another preferred method of delivering TGF-$\beta$ to the bony site is by way of TCP, including TCP ceramic blocks as described above and TCP particles, which encompass, for example, granules and powder. While the particles generally can be any size, the preferred particle size of TCP in this invention is >5 $\mu$m, more preferably greater than or equal to about 75 $\mu$m. More preferably, the size of the TCP granules is about 120–420 $\mu$m, most preferably about 125–250 $\mu$m, to obtain a granular putty that can be applied to defects that are not so wide as to require implants. The TGF-$\beta$ is typically adsorbed onto the TCP.

The amount of TCP employed will depend mainly on the type of mammal being treated and the size of the defect. In humans, the amount of TCP could reach up to about 50 g. The amount of TGF-$\beta$ would increase proportionately to TCP. Generally, the amounts range from about 0.5 $\mu$g to about 5 mg TGF-$\beta$, preferably about 1 $\mu$g to about 3 mg TGF-$\beta$, more preferably about 5 $\mu$g to about 1 mg TGF-$\beta$, adsorbed onto about 140 mg to about 50 g TCP particles, preferably granules. The amount of TGF-$\beta$ will be adjusted downward in accordance with conventional clinical parameters if there is a biphasic response in which the efficacy of the TGF-$\beta$ decreases with increasing TGF-$\beta$ concentration for the same size defect.

Optionally the formulation of TGF-$\beta$ and TCP also contains a polymer designed to bind the components together to improve consistency and ability to mold the resultant putty- or pastelike material. Examples of such polymers include, but are not limited to, amylopectin, gelatin, collagen, agarose, dextran, or a mixture of any two or more of these polymers. Further, the formulation suitably comprises the polymer in conjunction with a co-solvent such as glycerol, for example, gelatin and glycerol if the formulation is to be lyophilized before contact with the TCP and TGF-$\beta$ mixture.

The polymer is present in the composition in an amount that depends mainly on the size of the TCP particles being employed, as well as on the type of polymer utilized and the amount of TGF-$\beta$ and TCP used.

The TGF-$\beta$ and TCP may be first mixed before exposure to the polymer, or they may all be mixed together at the same time, or the TGF-$\beta$ may be mixed with the polymer and then with TCP. In a preferred mode, the TGF-$\beta$ and TCP are first mixed before the polymer is used to bind the mixture.

A particularly preferred binding polymer herein is amylopectin, especially in combination with TCP granules. The method of preparation of the amylopectin/TCP formulation, and possibly other TCP formulations, can be dependent on the size of the TCP particles employed. Thus, for example, if the size of the TCP particles is less than about 100 μm, the ingredients may be contacted in any order, including simultaneously mixing the TGF-β with the amylopectin and TCP or adding the TCP to the amylopectin followed by the TGF-β. However, if the size of the TCP granules is greater than about 100 μm, the order of mixing ingredients may affect the efficacy, at least in one animal model, and thus a preferred method of producing a bone-inducing formulation of TGF-β for all sizes of TCP granules, and particularly for larger sizes, comprises admixing an effective amount of a liquid solution of the TGF-β with the TCP granules for a sufficient period of time to adsorb the TGF-β onto the granules and contacting the resulting mixture with an effective amount of amylopectin. Conditions that ensure adsorption of the TGF-β on the TCP particles are exposing the TCP to the TGF-β at a temperature above about 0° C., preferably at least about 5° C., more preferably about 5°–40° C., still more preferably about 5°–30° C., and most preferably about room temperature. The time of exposure to TGF-β is preferably not less than about 5 minutes, although shorter times may be possible. Then the amylopectin is added and mixed manually with the powder to homogeneity.

A preferred composition comprises about 0.5 μg to 5 mg TGF-β, about 140 μg to 50 g TCP particles, preferably granules, and an amount of amylopectin that ranges from about 0.1:1 to about 1:1 (weight/weight) amylopectin: TCP, preferably 0.25:1 to 0.5:1 amylopectin:TCP, depending on the size of the TCP particles. Thus, if the TCP particles are less than 5 μm, the ratio of amylopectin to TCP is preferably about 0.25 to 1, and if the TCP particles are greater than or equal to 75 or 125 μm, the ratio of amylopectin to TCP is preferably about 0.5 to 1, and the ratio of TCP: amylopectin: TGF-β solution is most preferably 1:0.5:0.5.

The amylopectin may be obtained from any source of starch, such as corn and potato, with potato being preferred. The amylopectin is preferably sterilized before use, as by autoclave or irradiation. To minimize the number of colony forming units (CFU) the amylopectin is suitably dissolved in water to form a solution of about 2–4% and then sterilized by autoclave (about 100°–120° C. for no less than about 30 minutes). To remove all the water, it is also preferably lyophilized or spray dried.

The composition herein also may suitably contain other peptide growth factors such as IGF-I, TGF-β, human growth hormone, epidermal growth factor, and PDGF, provided that such factors do not include the bone morphogenetic factors defined above. Such growth factors are suitably present in an amount that is effective for the purpose intended, i.e., to promote formation of bone.

The invention will be more fully understood by reference to the following examples. They should not, however, be construed as limiting the scope of the invention. All literature citations are incorporated by reference.

EXAMPLE 1

The TGF-β1 used herein was the recombinant expression product of transfected human 293 cells as described by EP 200,341, supra, and by Derynck et al., *Nature*, supra, and purified as described in Derynck et al., *Nature*, supra. The individual samples of recombinant human TGF-β1 (rhTGF-β1) were sterilely prepared in methylcellulose containing 20 mM sodium acetate buffer at pH 5.0 and applied as a single topical dose. Selected concentrations of rhTGF-β1 were mixed with methylcellulose gel so that the final concentration of methylcellulose was 3%. The vehicle was formulated in a similar manner without rhTGF-β1 as a control. The material was stored at 5° C. until use.

The rat incisional model utilized young adult Simonsen Albino rats (300–350 g). Full thickness skin incisions were made by cutting through the subdermal panniculus carnosus musculature following application of Betadine TM brand antiseptic and 70% alcohol scrubbing to disinfect the surgical site. Two pairs of symmetrical transverse incisions (approximately 2.5 cm) were placed in each animal. A single dose of rhTGF-β1 in methylcellulose was placed into each stainless steel sutured wound by inserting a 25-gauge needle along the edge of the wound and below the sutures. The volume of rhTGF-β1 in 3% methylcellulose placed into each wound was 0.05 ml. Each rat had two incisions into which rhTGF-β1 in 3% methylcellulose was applied. One incision received either vehicle alone (3% methylcellulose) or no treatment at all. Concentrations of rhTGF-β1 were 500, 1000, 2000, or 4000 ng/ml. Dose response curves were developed using dose ranges of 5 to 10,000 ng/wound. Animals were euthanized on day 5, 7, 10, 14, 21, and 28. The entire dorsal skin was excised after the sutures were removed. Two 8-mm wide strips of skin were collected from each incision and fixed in 10% neutral buffered formalin for seven days.

New Zealand white male rabbits (2.5–2.8 kg) were purchased from Elkhorn rabbitry. Anesthesia was induced by an intramuscular injection of ketamine hydrochloride/xylazine hydrochloride mixture. After removal of hair from the ears, the area of the wound was sterilely prepared using Betadine TM brand antiseptic with an alcohol rinse. A circular 6-mm punch biopsy instrument was used to produce wounds to the depth of the ear cartilage. The underlying perichondrium was removed with a periosteal elevator and fine scissors. Wounds were treated with 0.025 ml of 3% methylcellulose or 5, 15, 25, 100, 500, or 1000 ng of rhTGF-β1 in 3% methylcellulose (control). Opsite TM surgical dressing was placed over each wound. An Elizabethian collar was placed around the neck of the rabbits to prevent mechanical disruption of the wounds by the rabbit.

Studies were also designed to examine short-term and long-term effects of topical rhTGF-β1. Wounds were harvested on days 3, 5, 7, 14, 21, 28, 42, 56, and 70. Wounds were photographed, cut into hemisections, and fixed in 10% neutral buffered formalin for histology and morphometric analysis. Morphometric analysis included measurements of total healing wound area, closing wound area, upper wound gap, lower wound gap, area of collagen, area of granulation tissue, epithelial cell layer length, and bone formation. These measurements were made on a BioQuant IV TM (R & M Biometrics Inc., Nashville, Tenn.) computer image analysis system.

The rabbit ear ulcers were examined for delayed effects of rhTGF-β1 on days 21, 28, 42, 56, and 70 following a single application of 25 or 100 ng/wound on the day of wounding. Bone formation was observed along the wound edges and immediately adjacent to the cartilage. The bone was normal in morphological appearance, consisting of endochondral or membranous type bone and ossification with marrow spaces. Osteoblasts and osteoclasts were present. The percentage of wounds with bone increased to a maximum of 74% of the treated wounds at day 42 (100 ng/wound) and decreased to 69% by day 70. See FIG. 1. Bone formation was observed in less than 12% of placebo-treated wounds.

No bone formation was observed in the rat incision model, indicating that bone formation is induced only at a site that has a source of precursor (osteogenic) cells, in this case in the rabbit ear model where the wound was adjacent to perichondrium.

EXAMPLE 2

A rat femur gap model was employed wherein a polyethylene plate 2-mm thick, 8–10 mm long, and 4–5 mm wide was pinned to one face of a rat femur with stainless steel pins. From the center of the femur a 5–8-mm long piece of bone was removed. The plate serves to keep the gap in bone separated. This model is intended to mimic a non-union fracture in a human.

Set into the gap in the femur is a porous cylindrical 200-to 400-micron ceramic implant of 60% by weight hydroxyapatite and 40% by weight TCP (Zimmer, Inc.), which is either (1) implant alone, (2) implant presoaked for 1 hour in a solution of 50 ng/ml rhTGF-$\beta$1 prepared as described in Example 1 and formulated in Delbecco's medium without serum, (3) implant plus dispersed whole bone marrow cells obtained from syngeneic rat, and (4) implant plus dispersed whole bone marrow cells pretreated with 50 ng/ml of the rhTGF-$\beta$1 in Delbecco's medium described above. A total of 15 rats were used for each of these four groups. One month after implant, the rats were sacrificed and analyzed for histological changes.

Preliminary results indicate that no bone replacement was observed in the control without cells or rhTGF-$\beta$ nor with rhTGF-$\beta$ without cells; TGF-$\beta$ with cells was found to accelerate the rate of bone growth over cells alone. The bone formed with rhTGF-$\alpha$ was found in the interstices of the pores in the ceramic and bridged the gap. The bone formed with the rhTGF-$\beta$ was found to be histologically normal.

EXAMPLE 3

A case study was performed using baboons to investigate the effect of TGF-$\beta$ on bone wound healing. The baboon was selected because of the close analogy of its bone kinetics to those of man. A methylcellulose gel of TGF-$\beta$1 was delivered via an analytical bone implant, and after 22 days the implant was removed from the baboon. Tissue obtained from TGF-$\beta$ implant sites was analyzed using quantitative histomorphometry to determine the mean effect of TGF-$\beta$ on bone wound healing. Detailed non-quantitative histopathologic evaluation was also performed.

More specifically, four male baboons were implanted with four titanium analytical bone implants (cages) each, two per tibia in areas of close structural geometry. Holes were drilled in the tibia to allow implantation. After implantation, the baboons were allowed to heal for 41 days. On the 41st day, all the implant sites were surgically exposed, tissue was removed, and the test materials were implanted into the implant cores. Each animal received a normal (no treatment) control, a control with only methylcellulose vehicle, and a low (1 $\mu$g rhTGF-$\beta$ in methylcellulose) or high (10 $\mu$g rhTGF-$\beta$ in methylcellulose) dosage of active TGF-$\beta$. Specifically, these formulations each consisted of 1 g of 3.0% methylcellulose by weight, lactic acid QS to pH 5.0, and 0, 20, or 200 $\mu$g/ml of rhTGF-$\beta$1 prepared as described in Example 1. The formulations were poured into size 5 gelatin capsules (Elanco), which were then placed in the core of the titanium implant and used to deliver 50 $\mu$l of each formulation, with slow dissolution of the capsule. All implant sites within an animal were randomly assigned to one of the four treatments.

Following 22 days of healing, tissue in all implants was retrieved. The tissue samples were placed in 10% formalin solution, buffered to a pH of 7.0, containing formaldehyde at 3.7% for fixation. Samples were submitted for histopathologic analysis.

The following descriptive and quantitative observations were made:

1. Bone volume in TGF-$\beta$ sites was lower than control and placebo sites, although not statistically significant.
2. Osteoblast numbers, volume, and activity were significantly greater in the TGF-$\beta$ sites when compared to either the control or placebo.
3. Osteoclast numbers and activity appeared higher in all four treatment sites when subjectively compared to control data obtained in previous studies.
4. Residual methylcellulose was noted and appeared to require phagocytosis before new trabecular bone could form.
5. TGF-$\beta$ in the presence of methylcellulose matrix was associated with increased numbers of fibroblast, osteoprogenitor cells, and osteoblasts.
6. No foreign body response or other adverse pathologic reaction to either matrix alone or matrix and TGF-$\beta$ was observed.
7. Significant periosteal new bone formation was noted over the implants in five TGF-$\beta$ sites in three animals. Bone formation over the implant to this degree had never been observed in over 450 titanium implant procedures carried out over the past few years.
8. TGF-$\beta$ sites were identified during blinded histologic review in seven out of a total of eight sites.
9. Methylcellulose sites were identified during blinded histologic review 100% of the time.

Control samples analyzed in this study demonstrated that cancellous tissue formed in the titanium implant is stratified from inferior to superior aspects of the implant core. The superior portion of the tissue (closest to the cap of the titanium implant) is less mature and shows greater osteoblastic activity, while tissue near the inferior aspects of the implant and deep within the medullary compartment is more mature in morphology and shows a reduced osteoblastic population and activity. In contrast to historical and control samples, the TGF-$\beta$ tissue samples were homogeneous in their high osteoblastic activity throughout the specimen.

Clinical observations of the tissue above and around the supra-periosteal portion of the titanium implant revealed pronounced periosteal bone formation. This periosteal bone formed large masses over two sites in each of two animals. The masses in these two animals were highly vascularized, had the clinical appearance of trabecular bone, and varied in size within one animal. The two masses in each of two animals were approximately 3×2×1.5 cm and 1.5×1×0.5 cm in size. One additional animal demonstrated pronounced periosteal bone formation over one TGF-$\beta$ site. It is significant that in over 450 titanium implant surgical procedures masses like these have never formed over the titanium implants. Histologically, this periosteal bone formation over five TGF-β sites in three baboons was similar to an actively healing, uncomplicated, fracture callus, i.e., morphologically normal, mature bone formation.

In general, the methylcellulose was well tolerated and no foreign body response was present in any of the four treatment sites. Additionally, no evidence of cytologic atypia or malignancy was found in either titanium implants or periosteal samples.

EXAMPLE 4

Introduction

The purpose of this study was to evaluate the effects of TGF-$\beta$1 in the rabbit skull defect model of bone formation when incorporated into a TCP matrix that was configured as a thin disc the approximate size of the defect (12 mm). This was accomplished by measuring selected bone morphometric parameters from stained histologic sections as well as by radiographic examination of the excised defect site. Results were compared to defects administered TCP discs without TGF-$\beta$1.

Source and Preparation of TGF-$\beta$1 and TCP Discs

The rhTGF-$\beta$1 was prepared and purified as described in Example 1. Individual samples of the active portion of rhTGF-$\beta$1 were prepared under sterile conditions in 20 mM sodium acetate buffer at pH 5.0. The incorporation of rhTGF-$\beta$1 into TCP discs (obtained from DePuy, Warsaw, Indiana) was done by aseptically incubating TCP in the TGF-$\beta$1 solution for three hours at room temperature. Prior to the incubation, TCP discs were sterilized by incubating in 70% ethanol, rinsing thoroughly with sterile normal saline, and drying under UV lamp. The average weight of each disc was 153 mg. Two different concentrations of rhTGF-$\beta$1 were used, 20 and 100 $\mu$g/ml. After incubation, each disc was rinsed briefly with sterile normal saline. The amount of rhTGF-$\beta$1 adsorbed onto the TCP disc was determined from the changes in the concentration of TGF-$\beta$1 incubating solutions by conventional ELISA methods. The higher concentration (100 $\mu$g/ml) gave the average value of 16 $\mu$g/disc, while 5 $\mu$g/disc was the average value from the incubation of the discs with 20 $\mu$g/ml TGF-$\beta$1.

Animal Surgery and Treatment

All studies were performed in accordance with the American Association for the Accreditation of Laboratory Animal Care (AAALAC) guidelines. Sixteen male New Zealand White rabbits (2.8–3.2 kg) (Elkhorn Rabbitry, Watsonville, Calif.) were anesthetized with 0.75 ml/kg Hypnorm® brand anesthesia (Jenssen Pharmaceutica, Beersa, Belgium). The top of the head and base of the ears were shaved and aseptically prepared for surgery. An elliptical incision was made over the skull, reflecting the skin flap anteriorly. Similarly, the periosteum was reflected anteriorly as a flap, exposing the top of the skull. Both skin and periosteal flaps were covered with sterile, moistened gauze. A 12-mm skull defect was selected since, in the absence of treatment, bone does not bridge the gap, but rather a fibrous tissue non-union of the skull persists. Frame, *J. Oral Surg.*, 38: 176–180 (1980). A sterile trephine attached to an electric drill was used to produce the defect at the point of intersection between the sutures of the right and left parietal and frontal bones. The site was liberally irrigated with physiological saline during the drilling to prevent overheating of the bone margins. Care was taken not to puncture or damage the underlying dura. A precut, sterile saline-moistened piece of Gelfilm TM brand of film (Upjohn, Kalamazoo, Mich.) was inserted through the defect overlying the dura to function as a barrier between the dura and the edges of bone.

Sterile TCP discs or TCP discs with rhTGF-$\beta$1 (5 or 16 $\mu$g) were applied to the defect filling the defect. The periosteal flap was sutured back in place with 6-0 proline sutures and the skin flap was closed with 4-0 silk. Rabbits were returned to their cages and allowed to recover. After 28 days rabbits were euthanized with an overdose of barbiturate and the defect sites were removed with adjacent normal bone. The defect sites were rinsed in physiological saline. Sites were fixed in 10% neutral buffered formalin and radiographed using a Faxitron TM brand X-ray system and X-omat AR-2 film exposed at 25 KV, 10 s. The fixed tissue samples were then cut in half at the center of the defect parallel to the frontal/parietal suture. One hemisection was acid decalcified (Easy-cut TM reagent, American Histology Reagent Co., Modesto, Calif.) and processed by routine histologic methods using hematoxylin and eosin to stain the 4-$\mu$m sections. The other half of the defect was plastic embedded, and undecalcified sections were processed by routine histologic methods, with the 5-$\mu$m sections stained with Goldners' trichrome, von kossa, or toluidine blue.

Goldner's trichrome stained sections were examined using a BioQuant IV TM computer image analysis system. Selected indices of bone formation and resorption were measured, including trabecular bone volume (TBV), percentage osteoid surface (%OS), percentage osteoid volume (%OV), mean osteoid width (OW), percentage osteoblast/osteoid (%Ob/Ost), percentage osteoblast/total surface (%Ob/TS), total resorption surface (TRS), and number (#) of osteoclasts/surface length (Oc/SL). Sections from all animals were analyzed histomorphometrically using a random stratified sampling scheme that systematically evaluated selected fields from the bony edge of the defect and the entire area within the defect. Fields were selected using a grid pattern, such that each field within the defect area had an equal probability of being selected. Approximately equal numbers of fields were evaluated for both the control and treated defects.

The thickness (width) of bone at the outside edge of the sections (at the edge of the harvested sample farthest from the defect site) was measured to evaluate the extent of bone formation at non-defect sites (non-defect end width, NEDW). Defect area that is normally quantitated radiographically using computer image analysis could not be determined accurately due to the radiopaque nature of the TCP discs.

Statistical analysis

Data were analyzed by one factor ANOVA and the Scheffe F-test to determine differences between groups. The test of significance was performed at the 95% confidence interval compared to vehicle control. Each group contained three to four rabbits.

Results

Figure 2:
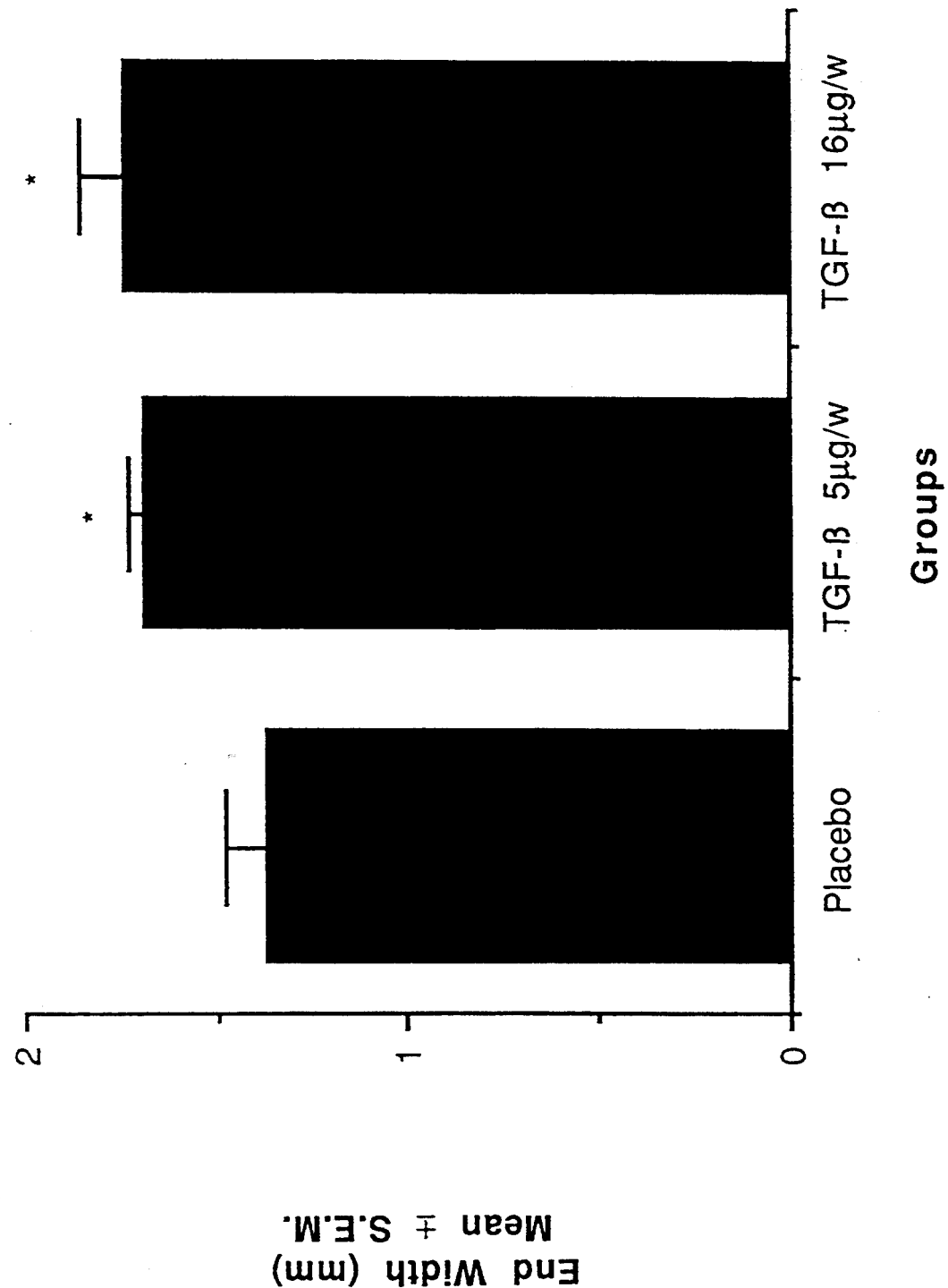
FIG. 2 illustrates the non-defect end width, an indication of the efficacy in the rabbit skull defect model, on day 28 post administration of placebo and TCP discs with rhTGF-$\beta$ adsorbed at two different concentrations, where * $p<0.05$.

Morphometric Evaluation. Data from the morphometric determinations are presented in Table 1. In general, TGF-$\beta$1-impregnated TCP discs stimulated a greater degree of bone formation at the defect site compared to TCP discs without TGF-$\beta$1. Indices of bone formation, including trabecular bone volume, osteoid width, osteoid volume, and osteoblast/osteoid were increased in the TGF-$\beta$1-treated defects compared to vehicle-treated defects. In addition, the number of osteoclasts/surface length and total resorption surface were increased in TGF-$\beta$1-treated defects compared to vehicle-treated defects, indicating that remodeling processes were present. Non-defect end width of bone from defects administered either 5 or 16 $\mu$g of TGF-$\beta$1 were greater than placebo-treated defects (see Table 1 and FIG. 2). The only parameters without significance between groups were osteoid surface and osteoblast/total surface.

TABLE 1

Histomorphometric Evaluation of Bone Formation in Skull Defects Applied TGF-$\beta$1 Impregnated onto TCP Discs[a]

| Histomorphometric Parameters[b] | Vehicle | TGF-$\beta$ 5 $\mu$g | TGF-$\beta$ 16 $\mu$g |
|---|---|---|---|
| TBV (%)   | 1.64 ± 0.83    | 21.60 ± 3.43[c]   | 15.59 ± 2.75[c] |
| OW (mm)   | 0.003 ± 0.003  | 0.01 ± 0.001[d]   | 0.009 ± 0.001[d] |
| OV (%)    | 0.76 ± 0.76    | 9.07 ± 2.17[c]    | 9.19 ± 0.73[c] |
| OS (%)    | 27.68 ± 27.68  | 46.59 ± 6.42      | 42.81 ± 4.30 |
| Ob/TS (%) | 36.44 ± 31.99  | 56.86 ± 5.04      | 65.69 ± 1.39 |
| Ob/Ost (%)| 40.14 ± 40.14  | 125.43 ± 8.56[d]  | 157.99 ± 15.34[d] |
| Oc/SL (#) | 0 ± 0          | 0.53 ± 0.09[d]    | 0.57 ± 0.20[d] |
| TRS (%)   | 0 ± 0          | 0.025 ± 0.005[d]  | 0.027 ± 0.009[d] |
| NDEW (mm) | 1.37 ± 0.11    | 1.69 ± 0.04[d]    | 1.75 ± 0.11[d] |

[a]Values reported are mean ± S.E.M. based. N = 3 for vehicle and 4 each for 5 or 16 $\mu$g of TGF-$\beta$1.
[b]TBV is trabecular bone volume; OW is osteoid width, OV is osteoid volume, OS is osteoid surface, Ob/TS is osteoblast/total surface, Ob/Ost is osteoblast/osteoid, Oc/SL is osteoclasts/surface length, TRS is total resorption surface, and NDEW is non-defect end width.
[c]$p < 0.01$.
[d]$p < 0.05$.

Due to the radiodense nature of the TCP discs, radiographic defect area was not determined. While there were apparent differences between placebo-treated and TGF-$\beta$1-treated defects, these differences were not amenable to morphometric determinations. However, the TGF-$\beta$1-treated defects appeared slightly more radiopaque, with the defect area and non-defect area blending without sharp border between the edge of the TCP disc and skull.

Histological evaluation, Histologic evaluation of the defects filled with TCP discs impregnated with TGF-$\beta$1 indicated an increase in the amount of bone surrounding the TCP disc. In addition, bone was observed migrating into the surfaces of the disc primarily at the margin of the defect, but also on the top and bottom surfaces. The new bone was characterized as a mixture of woven (immature) and lamellar (mature) bone by polarized light microscopic examination. In contrast, a minimal bony response was observed histologically in the TCP discs without TGF-$\beta$1.

In summary, the TCP discs impregnated with TGF-$\beta$1 induced a marked increase in bone both surrounding the discs as well as migrating into the discs. Bone was characterized histologically as a mixture of immature and mature bone indicating active formation and resorption processes. Remodeling of bone was subsequently confirmed histomorphometrically by an increase in both formation and resorption parameters within TGF-$\beta$1-treated sites. TCP discs without TGF-$\beta$1 were minimally inductive at 28 days with only slight amounts of bone located at the margins of the defect.

These data demonstrate that TCP will function as a carrier for TGF-$\beta$1 and provide a matrix on which bone can readily form across osseous defects.

EXAMPLE 5

Introduction

The purpose of this study was to evaluate the effects of TGF-$\beta$1 in the rabbit skull defect model of bone formation when incorporated into 40-100 mesh TCP matrix, wherein the TCP is supplied as granules. This was accomplished by measuring selected bone morphometric parameters from stained histologic sections as well as by radiographic examination of the excised defect site. Results were compared to defects administered 40-100 mesh TCP without TGF-$\beta$1.

Source and Preparation of TGF-$\beta$ and TCP Matrix rhTGF-$\beta$1 was prepared as described in Example 1. Individual samples of the active portion of rhTGF-$\beta$1 were prepared under sterile conditions in 20 mM sodium acetate buffer at pH 5.0. Two different concentrations of rhTGF-$\beta$1 were used, 25 and 100 $\mu$g/ml. Porous TCP granules were used (Peri-OSS ™ brand TCP, lot #7157EL2A2, 40-100 mesh; granules had the size of 150-420 $\mu$m and were supplied by DePuy and produced from TCP powder by isostatic pressing and then sintering). The total weight of TCP granules in each dose was 154 mg. The preparations were obtained by aseptically incubating, at 5° C. for two hours in a sterile filter unit, TCP particles in either 20 mM sodium acetate buffer, pH 5, or in the two TGF-$\beta$1 solutions of the same buffer.

After incubation, TCP granules were harvested by centrifugation to remove the liquid. The bathing solutions were then removed from the particles by microcentrifugation through a filter membrane. Samples that were treated with acetate buffer were labeled as placebo. Samples treated with 100 $\mu$g/ml of TGF-$\beta$1 were labeled as "high" dose and samples treated with 25 $\mu$g/ml of TGF-$\beta$1 were labeled as "low" dose. High dose, as indirectly determined by ELISA from the difference in the initial and the final bathing concentration, was 13.7±0.2 $\mu$g (±SD, n=3) and low dose was 2.9±0.1 $\mu$g (±SD, n=3). The average weight of TCP particles in each vial was 154.1±3.6 mg (±SD, n=8).

The amount of rhTGF-$\beta$1 adsorbed onto the TCP granules was determined from the changes in the concentration of TGF-$\beta$1 incubating solutions by conventional ELISA methods.

Animal Surgery and Treatment

The animal surgery and treatment were performed as described in Example 4. Sterile TCP or TCP with rhTGF-$\beta$1 (3 or 14 $\mu$g) was applied to the defect filling the defect. Radiography was performed as described in Example 4, and one hemisection was acid decalcified and one undecalcified as described in Example 4. Goldner's trichrome stained sections were examined using the BioQuant IV ™ computer image analysis system as described in Example 4. The thickness of bone at the outside edge of the sections was measured to evaluate bone formation at non-defect sites. In addition, defect area determined radiographically was quantitated using computer image analysis.

Statistical analysis

Statistical analysis was done as described in Example 4. Each group contained two to three rabbits.

Results

Figure 3:
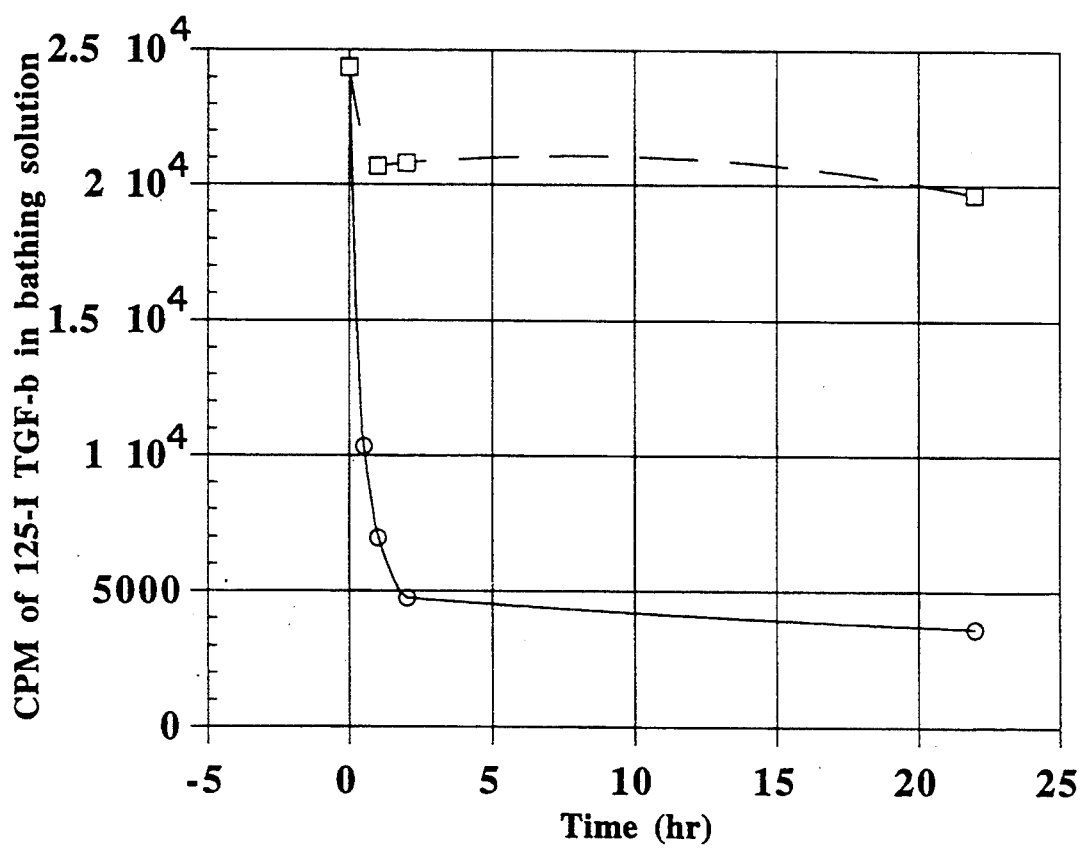
FIG. 3 illustrates the adsorption kinetics of TGF-$\beta$ in the presence of TCP granules (circles) and in the absence of TCP granules (squares).
Figure 4:
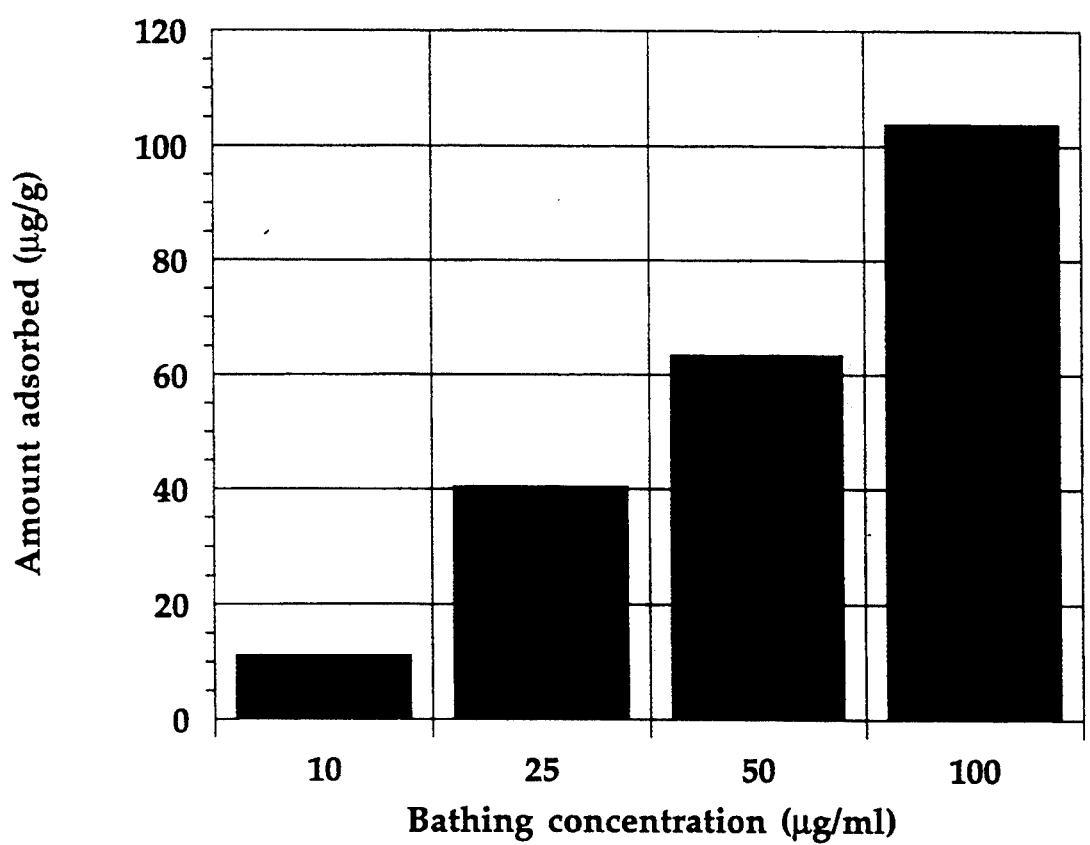
FIG. 4 discloses a graph of the amount of TGF-$\beta$ adsorbed on TCP granules as a function of the concentration of TGF-$\beta$ in the bathing solution.

Adsorption of TGF-$\beta$ onto TCP Granules. FIG. 3, which shows the adsorption kinetics of TGF-$\beta$ on TCP granules, indicates that after about 2 hours, the amount adsorbed appears to stabilize, with gradual change up to 22 hours. FIG. 4 shows the adsorption of TGF-$\beta$ on TCP granules, wherein the amount of TGF-$\beta$ adsorbed is given as a function of bathing concentration of TGF-$\beta$. It is seen that the amount of TGF-$\beta$ adsorbed increases proportionately to the amount of TGF-$\beta$ in the bathing solution.

Morphometric Determinations. Data from the morphometric determinations are presented in Table 2. In general, TCP with TGF-$\beta$1 stimulated a greater degree of bone formation at the defect site compared to TCP without TGF-$\beta$1. Indices of bone formation that were increased in defects administered TGF-$\beta$1 included osteoid width, % osteoid volume, % osteoid surface, and osteoblast/total surface. Trabecular bone volume, an indicator of the quantity of bone present within the defect, was significant only at p=0.06. Remodeling of bone was present as indicated by an increase in total resorption surface in the TGF-$\beta$1-treated defects compared to placebo-treated defects.

TABLE 2

Histomorphometric Evaluation of Bone Formation in Skull Defects Applied TGF-$\beta$1 Impregnated onto 40–100 Mesh TCP Granules[a]

| Histomorphometric Parameters[b] | Vehicle | TGF-$\beta$ | |
|---|---|---|---|
| | | 3 µg | 14 µg |
| TBV (%) | 1.09 ± 1.09 | 20.22 ± 5.40[c] | 26.18 ± 8.46 |
| OW (mm) | 0.002 ± 0.002 | 0.009 ± 0.001[c] | 0.008 ± 0.001[c] |
| OV (%) | 0.03 ± 0.03 | 9.67 ± 0.75[c] | 6.50 ± 2.22[c] |
| OS (%) | 1.39 ± 1.39 | 33.38 ± 2.66[c] | 34.14 ± 9.78[c] |
| Ob/TS (%) | 1.67 ± 1.67 | 33.42 ± 6.71[c] | 38.91 ± 8.28[c] |
| Ob/Ost (%) | 40.00 ± 40.00 | 98.83 ± 12.20 | 118.34 ± 7.65 |
| Oc/SL (#) | 0.33 ± 0.33 | 0.57 ± 0.07 | 0.65 ± 0.24 |
| TRS (%) | 0.006 ± 0.006 | 0.042 ± 0.015[c] | 0.041 ± 0.004[c] |

[a]Values reported are mean ± S.E.M. based. N = 3 for vehicle, 2 and 3 for 3 and 14 µg of TGF-$\beta$1, respectively.
[b]Abbreviations are defined in footnote b of Table 1.
[c]p < 0.05.

Figure 5:
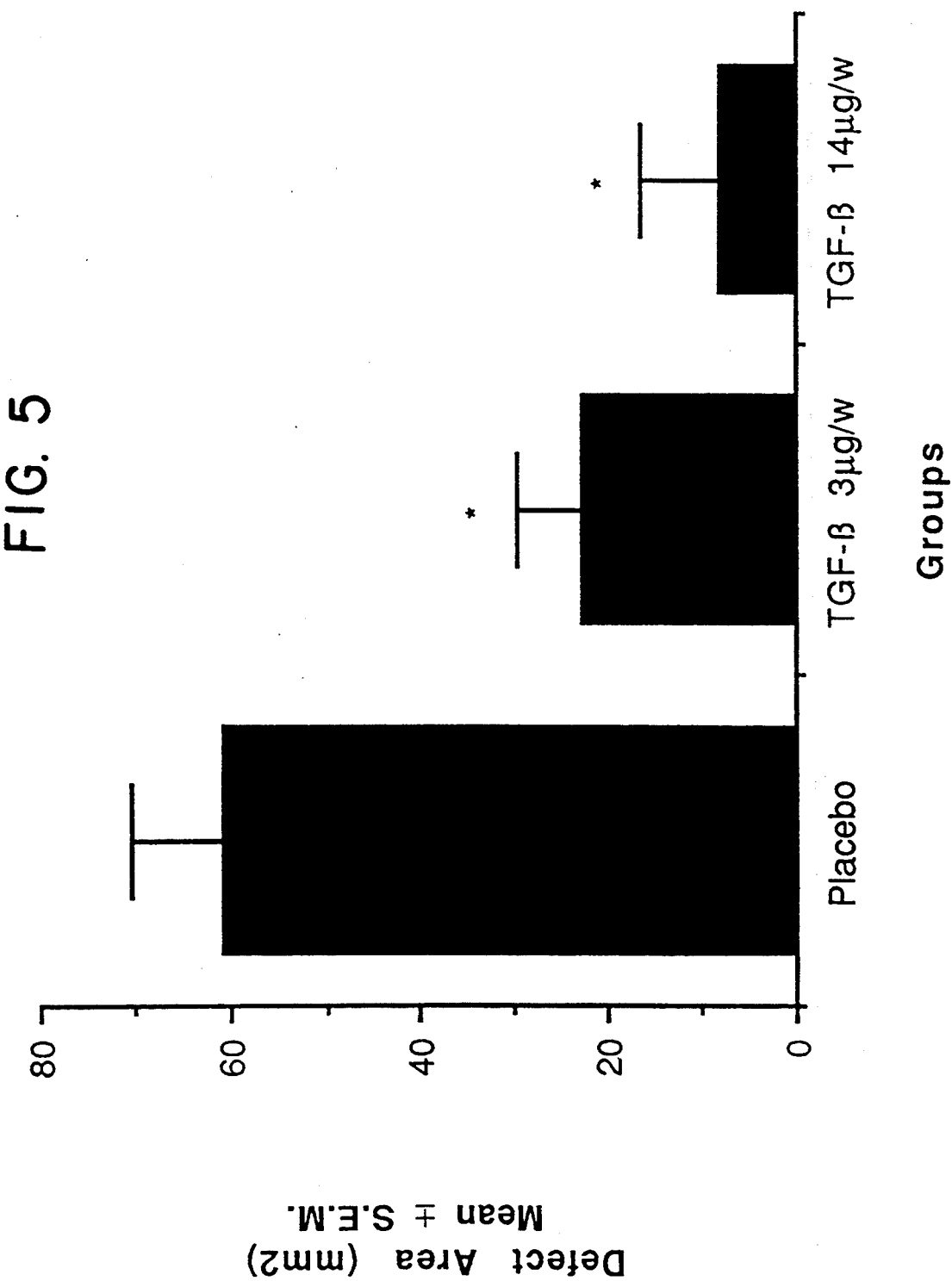
FIG. 5 illustrates the skull defect area in the rabbit skull defect model on day 28 post administration of placebo and TCP granules (40-100 mesh) with TGF-$\beta$ adsorbed at two different concentrations, wherein * $p<0.05$.

Radiographic defect area was determined using image analysis techniques. The defect areas were 60.57±9.69, 22.86±7.07, and 8.27±8.27 for placebo, 2 µg TGF-$\beta$1, and 14 µg TGF-$\beta$1, respectively (FIG. 5). The dose-responsive decrease in defect area was significant for both levels of TGF-$\beta$1 (p<0.05). In general, the placebo-treated defects were radiolucent and the TGF-$\beta$1-treated defects were radiopaque, except for small centrally located regions in the defects treated with 3 µg TGF-$\beta$1.

Histological evaluation. TCP granules (40–100 mesh) with TGF-$\beta$1 induced a variable response upon histologic examination. Generally, in defects administered TCP without TGF-$\beta$1, the predominant response was a mild chronic inflammation with a mixture of fibrous connective tissue bridging the defect and surrounding the granules of TCP. Minimal bone growth from the margins of the defect was observed in the control group. Defects administered TGF-$\beta$1 in TCP induced a much greater bone response with complete bridging in some cases. However, there was mild fibroplasia located within the central portion of the defect and surrounding TCP granules from defects administered 3 g of TGF-$\beta$1. Sometimes the bone formed over or around the granular area with the granules surrounded primarily by fibrous connective tissue. A similar response was observed in defects treated with 14 µg of TGF-$\beta$1, with less fibroplasia and more bone formation especially around the granules of TCP.

In summary, radiographs of defect sites after 28 days indicated complete defect closure with 14 µg rhTGF-$\beta$1 in 150 mg TCP, having induced a marked increase in bone both surrounding the dorsal and ventral region of TCP granules as well as migrating into the granules. The new bone formed within the defects was characterized histologically as a mixture of immature and mature bone. This indicates active formation and resorption processes that are natural to bone healing. Remodeling of bone was confirmed histomorphometrically by an increase in both bone formation and resorption parameters within TGF-$\beta$1-treated sites. The results indicate that the defect area is much lower after application of the TCP granules with 25 µg/ml (3 µg/wound site) TGF-$\beta$ and is even still lower after application of the TCP granules with 100 µg/ml (14 µg/wound site) TGF-$\beta$. TCP granules without TGF-$\beta$1 were minimally inductive at 28 days with only slight amounts of bone located at the margins of the defect.

These data show that TGF-$\beta$ in association with TCP without other carriers such as gelatin functions as a potent bone inducing growth factor, providing a matrix on which bone can readily form across osseous defects.

EXAMPLE 6

Introduction

The purpose of this study was to evaluate the effects of TGF-$\beta$1 in the rabbit skull defect model of bone formation when incorporated into TCP granules (150–420 µm) with 12% gelatin that was configured as a disc approximating the size of the defect (12 mm). This was accomplished by measuring selected bone morphometric parameters from stained histologic sections as well as by radiographic examination of the excised defect site. Results were compared to defects administered TCP in gelatin without TGF-$\beta$1.

Source and Preparation of TGF-$\beta$ and TCP Granules with Gelatin rhTGF-$\beta$1 was prepared as described in Example 1. Individual samples of the active portion of rhTGF-$\beta$1 were prepared under sterile conditions in 20 mM sodium acetate buffer at pH 5.0.

The solution of rhTGF-$\beta$1 in 12% gelatin was prepared by dissolving gelatin (type A, 300 Bloom grams) in 20 mM sodium acetate, pH 5.0 with moderate heat. The gel solution was sterilized by membrane filtration while it was still very warm. As the solution was cooled to a temperature below 50° C., an appropriate aliquot of the sterile rhTGF-$\beta$1 solution was added and homogeneously mixed. After mixing, 400 µl of this gelatin-TGF-$\beta$1 solution was pipetted into 5-ml vials that contained 300 mg of TCP granules (150–420 µm, DePuy). The preparation was allowed to congeal. By varying the added volume of TGF-$\beta$1 solution, the final doses were 0, 5, and 21.5 µg TGF-$\beta$1 per disc of TCP-gelatin.

Animal Surgery and Treatment

The animal surgery and treatment were performed as described in Example 4. Sterile TCP/gelatin or TCP/gelatin with TGF-$\beta$1 (5 or 21.5 µg) was applied to the defect filling the defect. Radiography was performed as described in Example 4, and one hemisection was acid decalcified and one undecalcified as described in Example 4. Goldner's trichrome stained sections were examined using the BioQuant IV TM computer image analysis system as described in Example 4. In addition, the defect area determined radiographically was quantitated using computer image analysis.

Statistical analysis

Statistical analysis was done as described in Example 4. Each group contained 5 to 6 rabbits.

Results

Morphometric Determinations. Data from the morphometric determinations are presented in Table 3. In general, TGF-β1 formulated in TCP and 12% gelatin stimulated a much greater degree of bone formation at the defect site compared to TCP in 12% gelatin without TGF-β1. All indices of bone formation were increased in defects administered either 5 or 21.5 μg TGF-β1. The number of osteoclasts/surface length and total resorption surface were increased in defects treated with 5 μg, but not 21.5 μg, TGF-β1, indicating that remodeling processes were present at least for the lower dose of the growth factor.

TABLE 3

Histomorphometric Evaluation of Bone Formation in Skull Defects Applied TGF-β1 in 300 mg TCP/12% Gelatin[a]

| Histomorphometric Parameters[b] | Vehicle | TGF-β | |
|---|---|---|---|
| | | 5 μg | 21.5 μg |
| TBV (%) | 0 | 14.11 ± 2.12[c] | 20.20 ± 4.09[c] |
| OW (mm) | 0 | 0.01 ± .001[c] | 0.01 ± 0.001[c] |
| OV (%) | 0 | 7.13 ± 0.99[c] | 8.34 ± 1.52[c] |
| OS (%) | 0 | 41.15 ± 3.01[c] | 50.38 ± 2.84[c] |
| Ob/TS (%) | 0 | 43.34 ± 6.28[c] | 57.34 ± 3.86[c] |
| Ob/Ost (%) | 0 | 104.37 ± 14.04[c] | 114.17 ± 5.34[c] |
| Oc/SL (#) | 0 | 0.47 ± 0.11[d] | 0.23 ± 0.11 |
| TRS (%) | 0 | 0.029 ± 0.009[d] | 0.012 ± 0.006 |

[a]Values reported are mean ± S.E.M. N = 5 for vehicle, and 6 each for 5 or 21.5 μg of TGF-β1.
[b]Abbreviations are defined in footnote b of Table 1.
[c]$p < 0.01$.
[d]$p < 0.05$.

Figure 6:
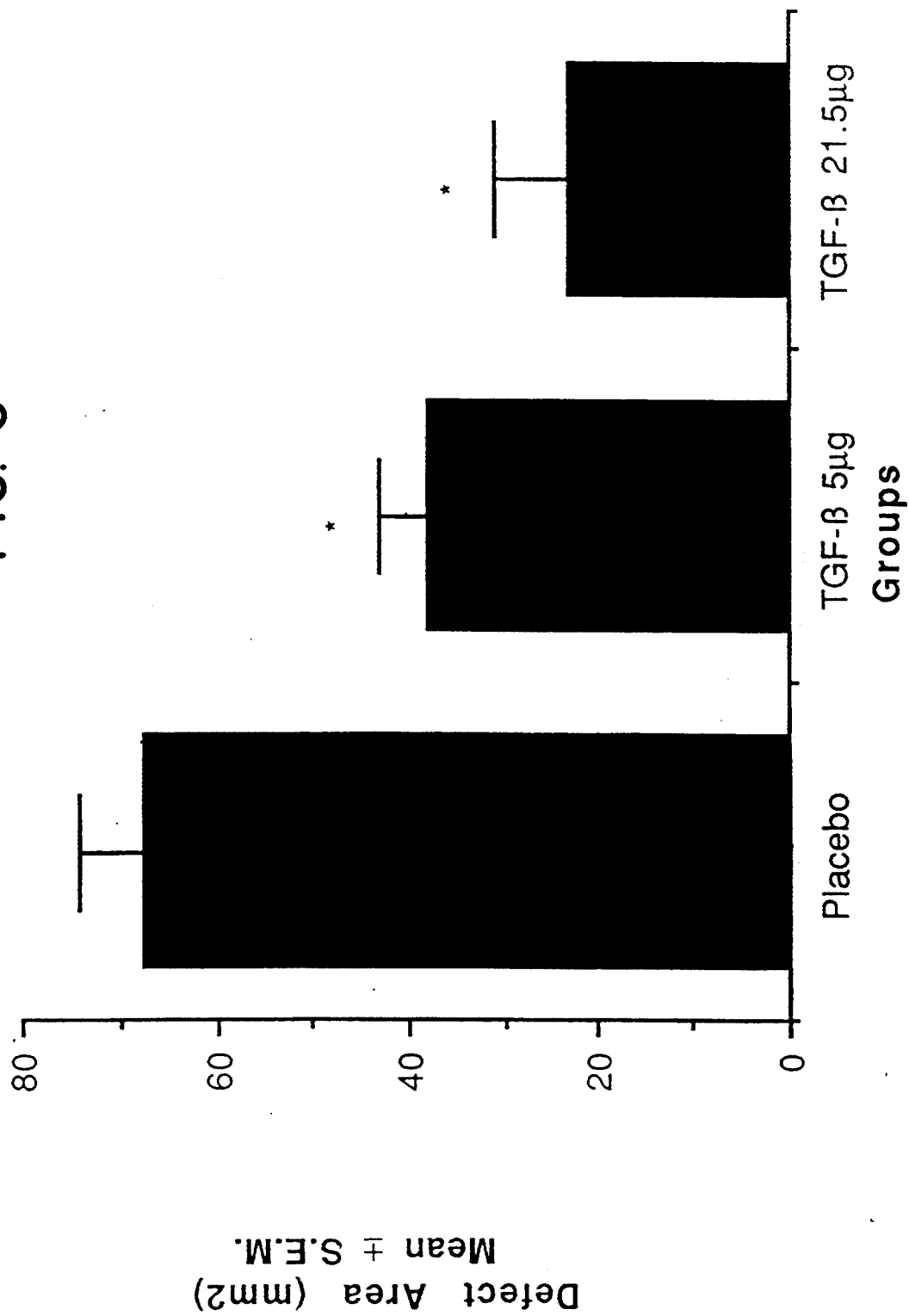
FIG. 6 illustrates the skull defect area in the rabbit skull defect model on day 28 post administration of placebo and TCP (300 mg)/12% gelatin with TGF-$\beta$ adsorbed at two different concentrations, wherein * $p<0.01$.

Radiographic defect area was determined using image analysis techniques. The defect areas were 67.49±6.57, 37.89±5.14, and 23.24±7.99 for placebo, 5 μg of TGF-β-1, and 21.5 μg of TGF-β-1, respectively (FIG. 6). The dose-responsive decrease in defect area was significant for both levels of TGF-β1 ($p<0.01$). Radiographs were difficult to interpret morphometrically since the granules of TCP were radiopaque. However, the general appearance of the TGF-β1-treated defects was denser, especially within the center of the defect.

Histologic Evaluation. TCP in 12% gelatin with TGF-β1 induced a variable response upon histologic examination. Generally, the predominant response was a mild chronic inflammation with a mixture of fibrous connective tissue bridging the defect and surrounding the granules of TCP in the defect administered TCP in 12% gelatin without TGF-β1. Minimal bone growth from the margins of the defect was observed in the placebo group. Defects administered TGF-β1 in TCP and 12% gelatin induced a much greater bone response with complete bridging in most defects administered 5 μg of TGF-β1. However, there was a mild chronic inflammatory response with fibroplasia located within the central portion of the defect and surrounding TCP granules from defects administered 5 μg of TGF-β1. Four of five defects administered 21.5 μg of TGF-β1 were completely bridged with bone. However, mild chronic inflammation in this group was still evident at each site with variable amounts of fibrous connective tissue intermingled with granules of TCP.

In summary, the TCP granules in 12% gelatin with TGF-β1 induced a marked increase in bone both surrounding the space occupied by the granules as well as interspersed in the granules. Bone was characterized histologically as a mixture of immature and mature bone, indicating active formation and resorption processes. Remodeling of bone was subsequently confirmed histomorphometrically by an increase in both formation and resorption parameters within TGF-β1-treated sites. When compared to the TGF-β1-impregnated TCP disc study, however, the values from histomorphometry were lower in the TCP granule/12% gelatin formulation, indicating that the bone response was not as vigorous. Also, the formulation melted rapidly and was not easily conformable to the defect.

These data demonstrate with the other examples that TCP will function as a carrier for TGF-β1 and provide a matrix on which bone can readily form across osseous defects. It is believed that the mild chronic inflammation would resolve with time as bone replaced the granules of TCP.

The same experiment is expected to yield similar results using a gelatin/agarose mixture containing, for example, about 0.05–1% (weight/weight) agarose, with an exemplary amount being 0.25%, to increase the melting point of the composition.

EXAMPLE 7

Introduction

The purpose of this study was to evaluate the effects of TGF-β1 in the rabbit skull defect model of bone formation when incorporated into TCP granules with 2% lyophilized gelatin that was configured as a disc of material approximating the size of the defect (12 mm). This was accomplished by measuring selected bone morphometric parameters from stained histologic sections as well as by radiographic examination of the excised defect site. Results were compared to defects administered large granules of TCP in lyophilized gelatin without TGF-β1.

Source and Preparation of TGF-β and TCP Particles and Gelatin rhTGF-β1 was prepared as described in Example 1 and formulated in TCP with 2% gelatin as follows. A solution of 2% gelatin (type A, 300 Bloom grams) with 2% glycerol was prepared in 20 mM sodium acetate, pH 5.0 and sterilized by filtration. An aliquot amount of sterile TGF-β1 solution (20 or 50 μg) was added into the gelatin mixture at a temperature of about 50° C. and homogeneously mixed at that temperature to form a gel solution. TCP particles (500 mg, sized at 420–2000 μm) were weighed into sterile siliconized vials. The gel solution (0.5 ml) was then added onto the TCP granules, sufficiently to cover all the granules. The preparation was subsequently lyophilized by conventional lyophilization technology. The final doses in these preparations were 20 and 50 μg.

Animal Surgery and Treatment

The animal surgery and treatment were performed as described in Example 4. Sterile large granules of TCP in lyophilized 2% gelatin without TGF-β (placebo) or with TGF-β1 (20 or 50 μg) were applied to the defect filling the defect. Radiography was performed and one hemisection was acid decalcified and one undecalcified as described in Example 4. Goldner's trichrome stained sections were examined using the BioQuant IV TM computer image analysis system as described in Example 4. The thickness of bone at the outside edge of the sections was measured to evaluate bone formation at non-defect sites. In addition, defect area determined radiographically was quantitated using computer image analysis.

Statistical analysis

Statistical analysis was done as described in Example 4. Each group contained four to five rabbits.

Results

Morphometric Determinations. Data from the morphometric determinations are presented in Table 4. In general, the baseline values for the placebo control group were relatively high, indicating that large granules of TCP in lyophilized gelatin induced bone formation to a greater extent than other formulations. However, 20 μg TGF-β1 stimulated more bone formation at the defect site compared to TCP in gelatin without TGF-β1 as indicated by an increase in trabecular bone volume and % osteoblast/total surface. In contrast, 50 μg TGF-β1 did not induce an increase in bone formation compared to the TCP placebo except for % osteoblast total surface. Non defect end width was similar between groups.

TABLE 4

Histomorphometric Evaluation of Bone Formation in Skull Defects Applied TGF-β1 with Large Granules of TCP in Lyophilized Gelatin[a]

| Histomorphometric Parameters[b] | Vehicle | TGF-β 20 μg | TGF-β 50 μg |
|---|---|---|---|
| TBV (%) | 15.66 ± 1.74 | 28.93 ± 2.65[c] | 15.43 ± 2.58 |
| OW (mm) | 0.011 ± 0.003 | 0.009 ± 0.001 | 0.009 ± 0.001 |
| OV (%) | 5.04 ± 0.58 | 7.31 ± 2.10 | 8.25 ± 1.23 |
| OS (%) | 30.27 ± 3.89 | 41.42 ± 6.68 | 40.68 ± 4.25 |
| Ob/TS (%) | 35.95 ± 2.24 | 50.47 ± 3.98[d] | 54.12 ± 4.84[d] |
| Ob/Ost (%) | 123.99 ± 11.03 | 129.62 ± 17.65 | 140.54 ± 22.04 |
| Oc/SL (#) | 0.32 ± 0.39 | 0.56 ± 0.16 | 0.33 ± 0.18 |
| TRS (%) | 0.015 ± 0.003 | 0.029 ± 0.009 | 0.017 ± 0.007 |
| NDEW (mm) | 1.55 ± 0.11 | 1.80 ± 0.12 | 1.90 ± 0.07 |

[a]Values reported are mean ± S.E.M. based. N = 5 for vehicle, 4 and 5 for 20 and 50 μg of TGF-β1, respectively.
[b]Abbreviations are defined in footnote b of Table 1.
[c]$p < 0.01$.
[d]$p < 0.05$.

Figure 7:
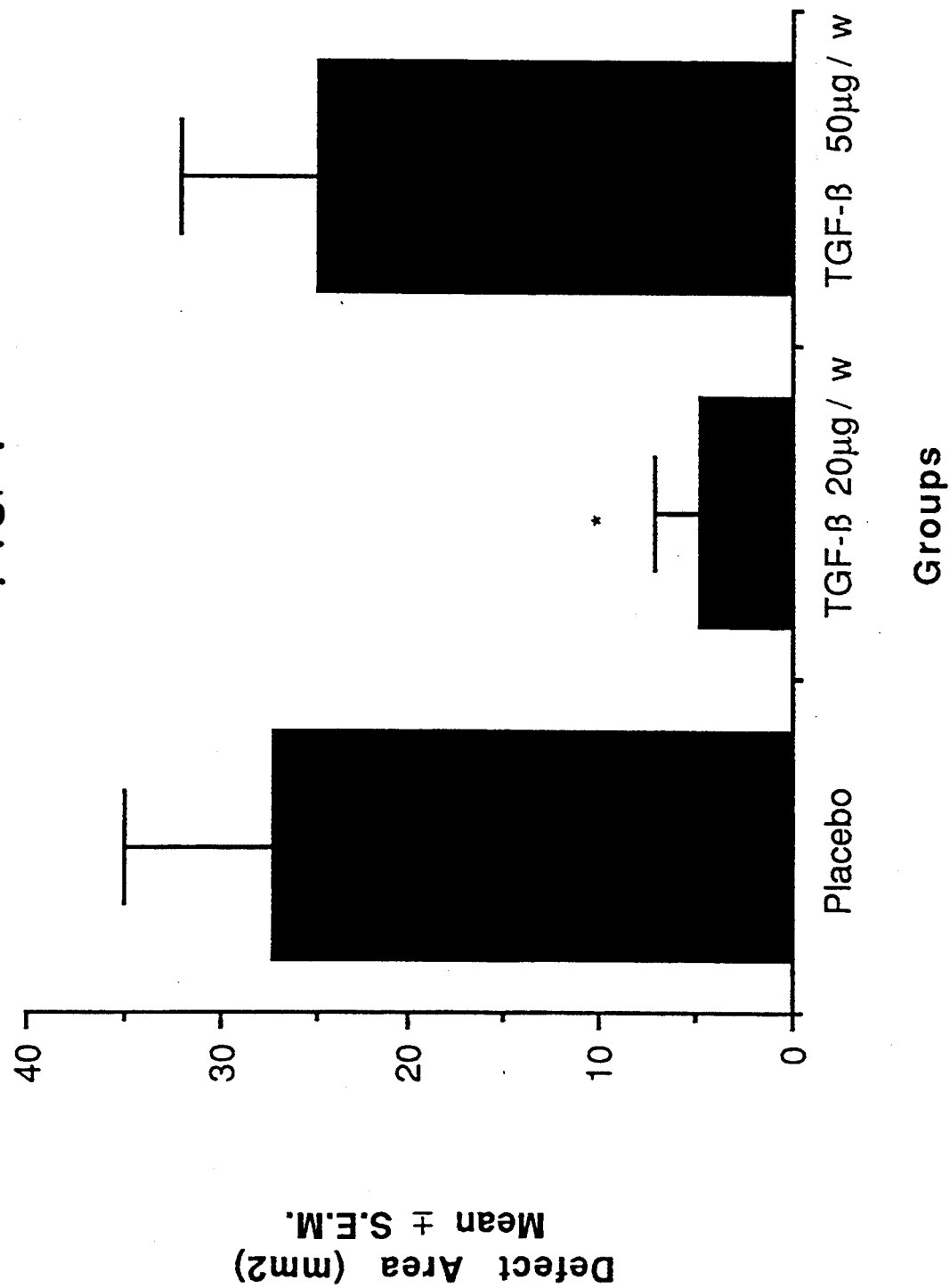
FIG. 7 illustrates the skull defect area in the rabbit skull defect model on day 28 post administration of placebo and TCP granules in lyophilized gelatin with TGF-$\beta$ adsorbed at two different concentrations, wherein * $p<0.05$.

Radiographic defect area was determined using image analysis techniques. The defect areas were 27.22±7.84, 4.86±2.25, and 25.01±7.06 for placebo, 20 μg TGF-β1, and 50 μg TGF-β1, respectively (FIG. 7). The decrease in defect area was significant for 20 μg of TGF-β1 only ($p < 0.01$). Radiographs were difficult to interpret morphometrically, since the large granules of TCP were radiopaque and unevenly distributed over the defect area. However, the general appearance of the defects administered 20 μg of TGF-β1 was denser and filled the defect.

Histologic Evaluation. Histologic examination of bone samples from defects administered TCP in lyophilized gelatin without TGF-β1 indicates bone formation at the margin of the defect bridging approximately 50% of the cross section. Where bone was present there appeared to be trabeculae of bone lined by osteoblasts surrounding the large granules of TCP. Marrow cavities were present with a typical cellular pattern for bone. In the central 50% of the defect from placebo-treated defects the large granules were surrounded by fibroblasts and fibrous connective tissue. Defects administered 20 μg TGF-β1 in large granules of TCP and lyophilized gelatin induced a much greater bone response with complete bridging in all cases. However, there were small areas of fibroplasia occasionally located within the central portion of the defect and surrounding TCP granules. Histologic examination indicated that defects administered 50 μg TGF-β1 induced a variable response. Two of five defects administered 50 μg TGF-β1 were completely bridged with bone, while 2 of 5 defects contained predominantly a fibrous response with minimal bone from the margins of the defect. In each case at 50 μg TGF-β1, there was a thick layer of fibrous connective tissue over the periosteal surface.

In summary, the large TCP granules in lyophilized gelatin with 20 μg TGF-β1 induced a moderate increase in bone both surrounding the space occupied by the granules as well as interspersed in the granules. Bone was characterized histologically as a mixture of immature and mature bone, indicating active formation and resorption processes. When compared to other formulations of TCP without TGF-β1, there was a substantial increase in the baseline amount of bone in the TCP placebo group. Without being limited to any one theory, this effect could be attributed to the size of the TCP granules, which are known to be conductive, as well as to the lyophilized gelatin formulation. The low dose of TGF-β1 (20 μg) induced an increase in bone compared to both the TCP placebo and 50 μg TGF-β1. While morphometrically there were fewer parameters that were significantly different from TCP placebo than in the other TCP studies, the low dose of TGF-β1 appeared very comparable to similar doses of TGF-β1 in other formulations. In contrast, 50 μg TGF-β1 was remarkably different, with a much greater degree of fibroplasia and a much more variable amount of bone. This indicates that in this model there is a biphasic response with TGF-β1 similar to other models of soft tissue wound healing.

These data further demonstrate that TCP will function as a carrier for TGF-β and provide a matrix on which bone can readily form across osseous defects.

EXAMPLE 8

The purpose of this study was to evaluate the effects of TGF-β1 in the rabbit skull defect model of bone formation when incorporated into TCP granules (5 μm or 250 μm nominal particle size) with amylopectin that was configured as a malleable putty approximating the size of the defect (12 mm). In addition, the individual components, i.e., TCP (5 or 250 μm) and two different lots of amylopectin were evaluated to determine which component contributed to the incidence of giant cell formation observed in this model. Defect sites were removed 28 days after surgery, radiographed, and processed for histomorphometric determinations.

Introduction

In the rabbit skull defect model, there appears to be a foreign body giant cell response. The purpose of this study was to evaluate in this model the effects of the individual components of the formulation and combinations of TGF-β1 and two sizes of TCP granules (nominal 5 or 250 μm granules) formulated in two lots of amylopectin having different levels of endotoxin present. Histologic examination with measurement of selected bone morphometric parameters from stained histologic sections as well as radiographic examination of the excised defect site were used as criteria for efficacy.

Source and Preparation of TGF-β1 and TCP/amylopectin

Types of Formulations tested, Eight groups of formulations were evaluated for efficacy in the animal model: two amylopectin controls, two vehicle controls, and the TGF-β1-treated groups as described below:

Group 1: Amylopectin with 12 EU/g
Group 2: Amylopectin with >3500 EU/g
Group 3: 5 μm TCP and amylopectin
Group 4: Amylopectin and 250 μm TCP
Group 5: Amylopectin and 10 μg TGF-β1

Group 6: Amylopectin and 5 μm TCP and 10 μg TGF-β1

Group 7: Amylopectin and 250 μm TCP and 10 μg TGF-β1

Group 8: 10 μg TGF-β1 and 250 μm TCP and amylopectin*

* Group 8 differs from group 7 only in the order of mixing.

Preparation of Formulations. rhTGF-β1 was prepared as described in Example 1. Individual samples of the active portion of the TGF-β1 were prepared under sterile conditions in 20 mM sodium acetate buffer at pH 5.0. Two different ranges of particle size of TCP were used to prepare the paste, 5 and 250 μm (nominal, range=5-45 μm and 250-500 μm, respectively). Aseptic conditions were maintained throughout the preparation procedure. The TCP granules were sterilized by 2.5 MRAD gamma irradiation.

Two lots of amylopectin (potato, Sigma Chemical Co.) with different levels of endotoxin (12 EU/g and >3500 EU/g) were used in Groups 1 and 2, respectively. Only the 12-EU/g amylopectin was used in Groups 3-8.

The TCP/amylopectin paste for Group 7 was prepared by mixing sterile TCP granules and sterile amylopectin in the ratio of 4:1 and 2:1 (by weight) for TCP granules with particle size of <45 and 250-500 μm, respectively. An aliquot of TGF-β1 solution in 20 mM acetate buffer, pH 5, was added to the solid mixture. The mixing was then performed manually using a spatula and plate until a uniform mass was obtained. In each preparation, the volume of TGF-β1 solution was kept constant at the ratio of 1:0.4 (weight of TCP: volume of TGF-β1 solution). The amount of amylopectin/TCP paste administered into each animal was about 500 mg, with the final dose of 10 μg TGF-β1.

For Group 8, the TGF-β solution was mixed with the TCP sufficiently to become adsorbed thereon, and then the amylopectin was mixed in to homogeneity.

Animal Surgery and Treatment

The animal surgery and treatment were performed as described in Example 4 using the eight groups of formulations defined above. The formulations were malleable, having the consistency of putty, and were applied to the defect filling the space completely. Radiography was performed as described in Example 4, and one hemisection was acid decalcified and one undecalcified as described in Example 4.

The decalcified and undecalcified stained sections were evaluated for general characteristics and quality of healing, especially for the presence or absence of a foreign body giant cell response. In addition, Goldner's trichrome stained sections were examined using the BioQuant IV ™ computer image analysis system as described in Example 4. In addition, defect area determined radiographically was quantitated using computer image analysis.

Statistical analysis

Statistical analysis was done as described above. Each group contained two to three rabbits.

Results

Histologic Evaluation. A summary of the histopathologic evaluation is presented in Table 5. Both lots of amylopectin induced a minimal bone response for foreign body giant cell response. In contrast, the amylopectin with 5 μm or 250 μm TCP granules induced a mixed response with minimal bone formation and a marked foreign body giant cell response. Defect sites administered amylopectin with 10 μg TGF-β1 but without TCP exhibited extensive new bone formation with minimal foreign body giant cell response. Ten μg TGF-β1 administered to defects with amylopectin and 5 μm TCP induced a variable response with new bone formation as well as a moderate giant cell response. When 10 μg TGF-β1 was mixed with 250 μm TCP and then mixed with amylopectin, the amount of bone formation was increased to a level similar to the growth factor plus amylopectin formulation and the degree of giant cell formation was minimal to moderate. In contrast, when the mixing order was reversed such that the TCP and amylopectin were mixed first, the TGF-β1 added less bone and a greater degree of giant cell formation occurred.

TABLE 5

Summary of Histologic Evaluation of Hematoxylin- and Eosin-Stained Sections

| Group | |
|---|---|
| 1 | Minimal bone response; connective tissue bridge; minimal giant cell response. |
| 2 | Minimal bone response; connective tissue bridge; minimal giant cell response. |
| 3 | Minimal to no bone response; very reactive, with numerous giant cells throughout. |
| 4 | Minimal to no bone response; moderate fibrosis; numerous giant cells surrounding large cavities (presumably decalcified TCP). |
| 5 | Complete bridging of defect with bone; profound increase in osteoblasts; minimal signs of chronic inflammation; thick fibrotic capsule overlying bone. |
| 6 | 75-90% bridging of defect with bone; central area contains moderate fibrosis; moderate giant cell response with lots of debris (small particles); bone looks good where it is present; in one sample the bone appears to be primarily periosteal with gaps at the original cut edges. |
| 7 | 0-90% bridging of defect with bone; ⅓ - severe giant cell response; small amount of connective tissue; ⅓ - center area moderate giant cell response with chronic inflammation; ⅓ - new bone looks good, funnels down centrally with mild giant cell response with debris. |
| 8 | 75-100% bridging of defect with bone; minimal (⅔) to moderate (⅓) giant cell response; thick fibrous response overlying bone; predominant response is one of large amounts of bone surrounding small cavities (decalcified TCP). |

Figure 8:
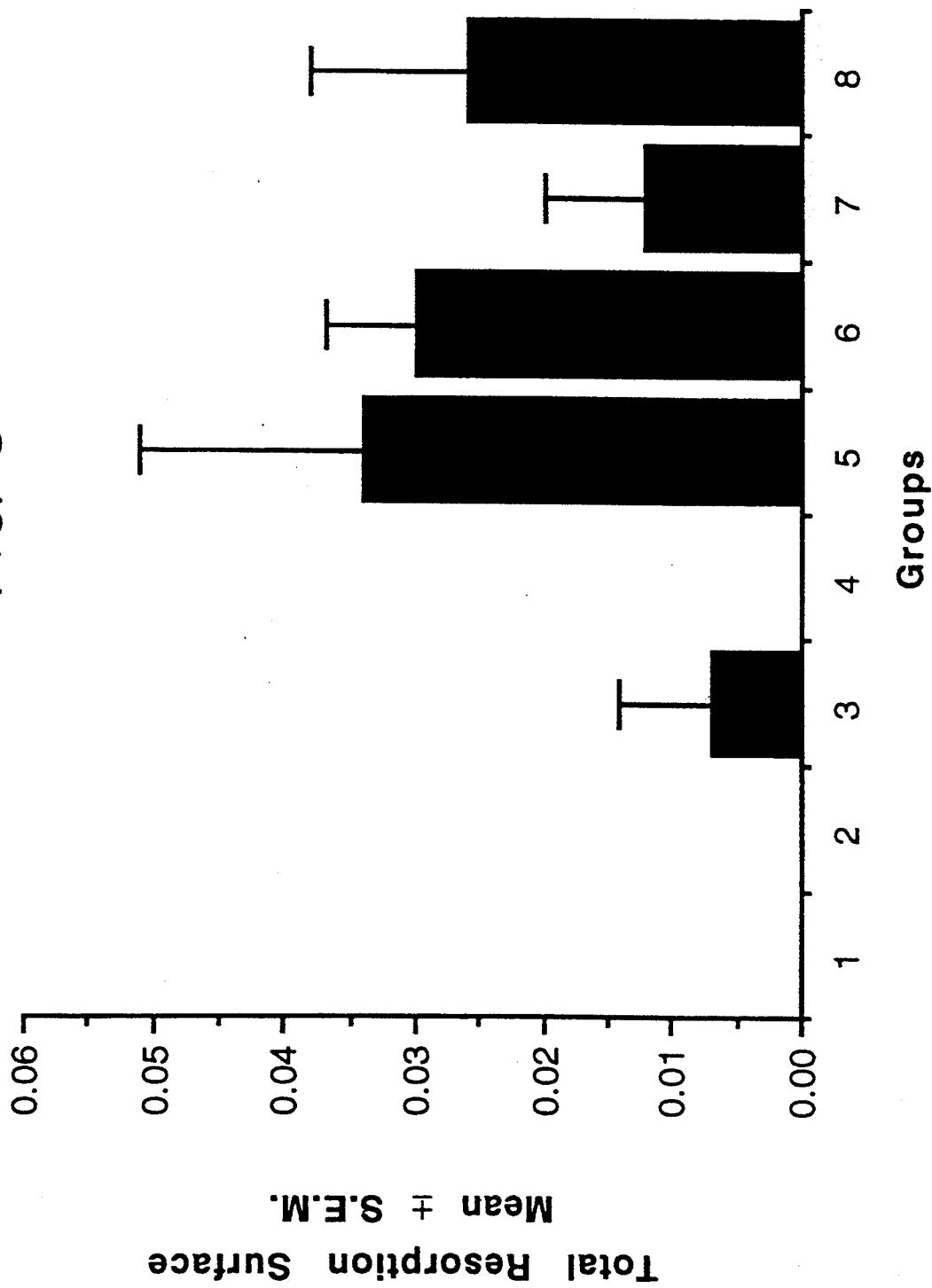
FIG. 8 illustrates total resorption surface in the rabbit skull defect model on day 28 post administration of a first lot of amylopectin with low endotoxin levels (1), a second lot of amylopectin with higher endotoxin levels (2), 5 $\mu$m TCP (3), amylopectin+250 $\mu$m TCP (4), amylopectin+10 $\mu$g TGF-$\beta$ (5), amylopectin+5 $\mu$m TCP+10 $\mu$g TGF-$\beta$ (6), amylopectin+250 $\mu$m TCP+10 $\mu$g TGF-$\beta$ (7), and 10 $\mu$g TGF-$\beta$+250 $\mu$m TCP+amylopectin (8).

Morphometric Determinations. Data from the morphometric determinations are presented in Table 6 and FIG. 8. No measurements could be determined in the vehicle groups that contained either lot of amylopectin. In general, TGF-β1 formulated with 250 μm TCP, then mixed with amylopectin, stimulated a much greater degree of bone formation at the defect site compared to the other formulations except for the TGF-β1 and amylopectin combination. Most osteoblastic and osteoclastic indices were increased in the TGF-β1-treated groups compared to groups without TGF-β1.

Figure 9:
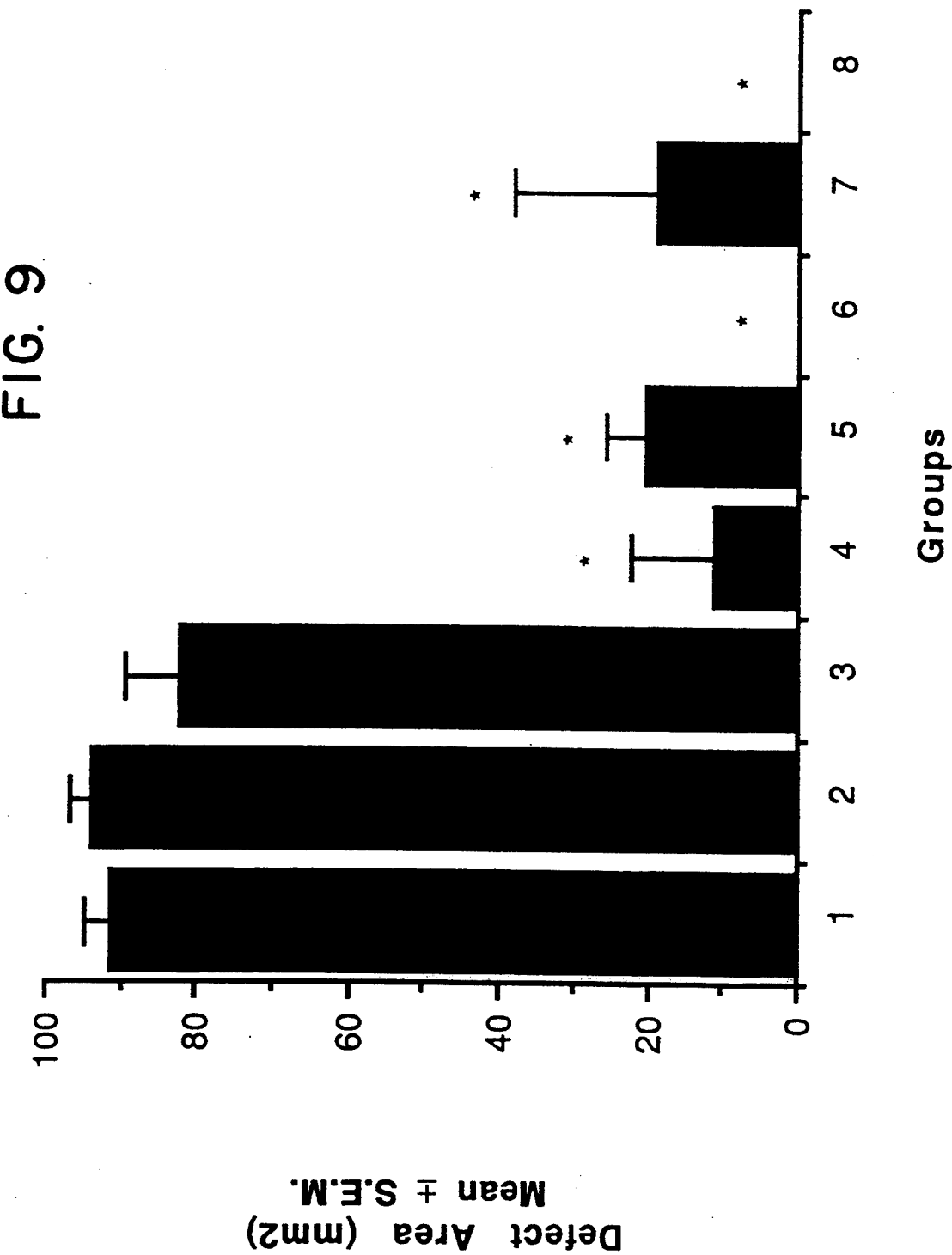
FIG. 9 illustrates the skull defect area in the rabbit skull defect model on day 28 post administration of formulations 1-8 defined in the legend to FIG. 8, wherein * $p<0.05$.

Radiographic defect area was determined using image analysis techniques and is illustrated in FIG. 9. The differences between groups typically depended on the presence or absence of TGF-β1. The defect area tended to be smaller for the non-TGF-β1-treated groups that contained TCP granules that were 250 μm. However, radiographs were difficult to interpret morphometrically due to the radiopacity of the TCP granules in all but the first two groups, i.e., the two lots of amylopectin alone.

TABLE 6

Histomorphometric Evaluation of Bone Formation in Skull Defects

Histomorphometric[a] Parameters

| Group | Trabecular Bone Vol. (%) | Osteoid Width (mm) | Osteoid Volume (%) | Osteoid Surface (%) | Osteoblast/ Total Surface (%) | Osteoblast/ Osteoid (%) | Osteoclast/ Surface Length (#) |
|---|---|---|---|---|---|---|---|
| 1 | 0 (0) | 0 (0) | 0 (0) | 0 (0) | 0 (0) | 0 (0) | 0 (0) |
| 2 | 0 (0) | 0 (0) | 0 (0) | 0 (0) | 0 (0) | 0 (0) | 0 (0) |
| 3 | 2.68 (2.68) | 0.003 (0.003) | 1.10 (1.10) | 5.41 (5.41) | 7.54 (7.54) | 46.40 (46.40) | 0.10 (0.10) |
| 4 | 2.27 (2.27) | 0 (0) | 0 (0) | 0 (0) | 25.01 (25.01) | 0 (0) | 0 (0) |
| 5 | 31.27 (1.28) | 0.01 (0) | 7.63 (1.42) | 49.56 (6.49) | 51.56 (9.26) | 102.51 (5.83) | 0.54 (0.27) |
| 6 | 16.71 (1.99) | 0.012 (0.004) | 12.06 (5.15) | 38.38 (11.39) | 52.90 (6.85) | 166.75 (48.83) | 0.46 (0.11) |
| 7 | 16.82 (8.54) | 0.014 (0.009) | 8.21 (6.04) | 22.41 (11.51) | 28.59 (14.30) | 86.9 (44.97) | 0.14 (0.07) |
| 8 | 30.78 (6.26) | 0.016 (0.002) | 13.20 (3.53) | 51.29 (7.02) | 45.33 (4.88) | 89.55 (6.73) | 0.40 (0.21) |

[a]Data are expressed as mean (S.E.M.).

In summary, results from this study indicate that the amount of endotoxin present in the amylopectin did not affect the amount of giant cell formation and therefore indicates that amylopectin should be an adequate carrier for TCP and TGF-β1. In contrast, both the 5 μm and 250 μm TCP induced giant cell formation when mixed with the low-endotoxin amylopectin. It was determined retrospectively that the 250 μm TCP contained TCP powder (particles <45 μm). Since the degree of giant cell formation was less in the 250 μm TCP than the 5 μm TCP, without being limited to any one theory, it is believed that the small TCP granules in the 250 μm TCP formulation may be contributing to the level of giant cell formation.

The defect area measured from radiographs was similar between groups administered amylopectin alone or 5 μm TCP granules alone. The defect areas for sites administered amylopectin and 250 μm TCP granules (with or without TGF-β1) were similar and all were smaller than sites administered 5 μm TCP granules alone or amylopectin alone.

Morphometric parameters were similar among the TGF-β-treated groups. Histopathologic examination of the eight microscopic slides indicates that the overall response of the TGF-β1 formulated in 250 μm TCP was better than that of the TGF-β1 formulated in 5 μm TCP. A moderate to severe giant cell foreign body reaction was observed with the 5 μm TCP in amylopectin with or without TGF-β1.

These data indicate that TCP/amylopectin will function as a carrier for TGF-β and provide a matrix on which bone can readily form across osseous defects.

EXAMPLE 9

The purpose of this study was to evaluate the effects of TGF-β1 in the rabbit long-bone model of bone formation when incorporated into TCP granules (5 μm or 250 μm nominal particle size) with amylopectin that was configured as a malleable putty the approximate size of the defect. Defect sites were radiographed and processed for histomorphometric determinations.

Source and Preparation of TGF-β1 and TCP/amylopectin rhTGF-β1 was prepared as described in Example 1. Individual samples of the active portion of the rhTGF-β1 were prepared under sterile conditions in 20 mM sodium acetate buffer at pH 5.0. A 4% solution of amylopectin (potato, Sigma Chemical Co.) was prepared by adding amylopectin to water and sterilizing in an autoclave at 100°–120° C. for no less than 30 minutes. The solution was filtered through a 0.22-μm membrane. For removal of all water, the sterile amylopectin solution was lyophilized.

The sterile TGF-β1 solution was adsorbed onto the TCP granules (125–250 μm) by aseptic incubation in a sterile filter unit at 5° C. for 2 hours as described in Example 5. The amylopectin was aseptically mixed with the TCP granules upon which the TGF-β1 solution was adsorbed using plate and spatula to homogeneity.

The proportions of amylopectin, TCP, and volume of water from the TGF-β1 solution were varied according to the particle size of TCP. In this study, three ranges of particle size were used, <5 μm, ≧75 μm, and ≧125 μm. The proportion (by weight) of TCP:amylopectin was 1:0.25 when the TCP particles were <5 μm. The percentage of water needed in the mixing was 30% (volume/weight of the total amount of solids). For TCP with larger particle sizes (≧75 μm and ≧125 μm), the ratio of TCP:amylopectin: TGF-β solution (weight/weight) was 1:0.5:0.5.

Release of TGF-β from TCP/Amylopectin Formulation

Figure 10:
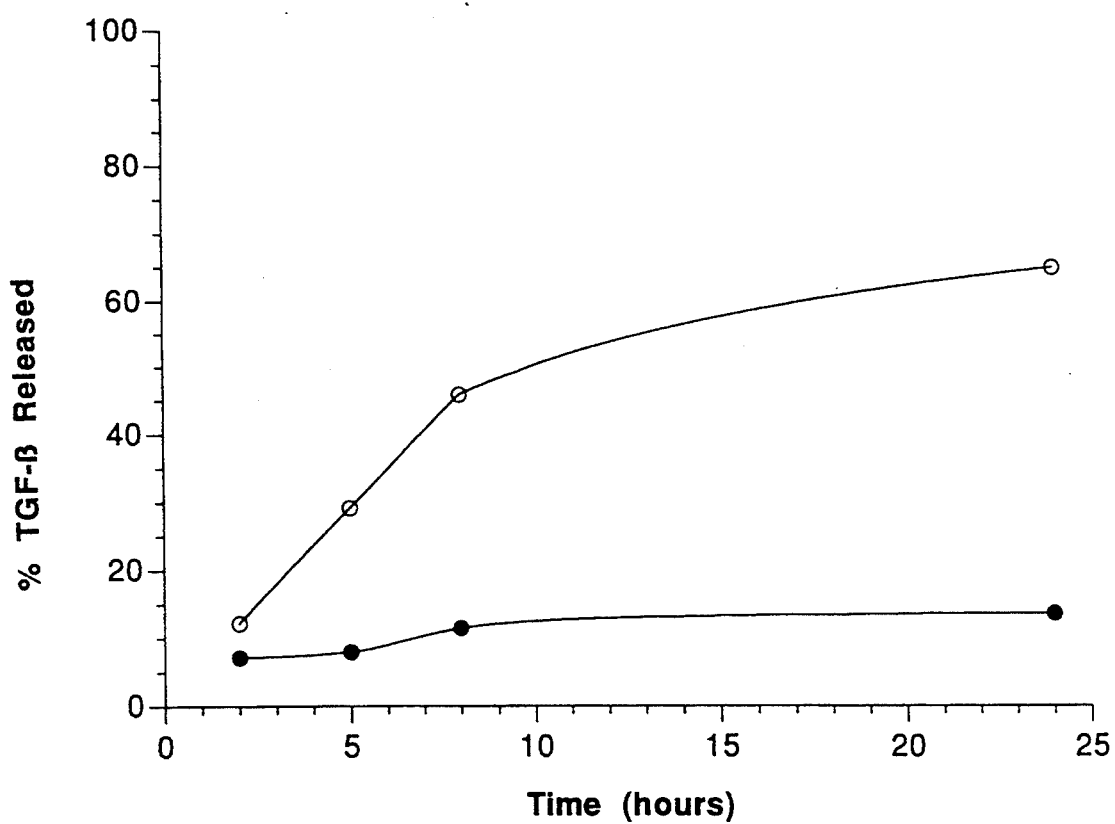
FIG. 10 illustrates release over time of TGF-$\beta$ from an amylopectin/TCP formulation as analyzed by ELISA, where the open circles are release into normal human serum and the solid circles are release into PBS/0.5% BSA.

FIG. 10 shows a graph of the percent of TGF-β released over time from the amylopectin/TCP formulation of 250 to 400 μm particle size into normal human serum (open circles) and into phosphate buffered saline (PBS) containing 0.5% bovine serum albumin (BSA) (solid circles). The release of the TGF-β was measured by standard ELISA methods. It can be seen that the TGF-β is released much more quickly from the TCP/amylopectin in normal human serum than in the PBS.

Animal Surgery and Treatment

A model of repair of long bone discontinuities in rabbits was devised based on that provided in Lemons et al., supra. All studies were performed in accordance with the AAALAC guidelines. Male New Zealand White rabbits (2.8–3.2 kg) (Elkhorn Rabbitry, Watsonville, Calif.) were anesthetized with 0.75 ml/kg Hypnorm® brand anesthesia (Jenssen Pharmaceutica, Beersa, Belgium). The right forelimb from each rabbit was shaved and aseptically prepared for surgery. An incision was made over the anterior-medial aspect of the forearm (radium/ulna), reflecting the skin laterally. The muscles surrounding the radius were bluntly reflected from the field of view and about 1.5 cm of the radius was exposed. A 10-mm section of the mid-shaft radius was removed using an electric drill while liberally irrigating with physiological saline during the drilling to prevent overheating of the bone margins. Care was taken not to damage the adjacent ulna. After the 10-mm section of bone was removed, the gap was packed with sterile gauze to facilitate hemostasis. The defect site was subsequently irrigated to eliminate any small particles of bone.

Three groups were evaluated in the initial preliminary investigations. The vehicle control group was treated with a formulation consisting of sterile TCP (125 μm particle size) mixed with amylopectin to homogeneity. The TGF-β1-treated group was treated with a mixture of TCP, amylopectin, and 15 μg TGF-β1 formulated as described above. The third treatment group consisted of a 10-mm defect without any treatment. The formulation with TGF-β1, amylopectin, and TCP was malleable, having the consistency of putty, and was applied to the defect filling the space completely. The reflected muscles were sutured back in place and the skin was closed with 4-0 silk. Rabbits were returned to their cages and allowed to recover.

Immediately after surgery and weekly thereafter, the surgical site from each rabbit was radiographed to monitor healing. After 28 days rabbits were euthanized with an overdose of barbiturate and the radius and ulna were removed and excess soft tissue (i.e., muscle) was dissected away from the bone and defect site. Sites were fixed in 10% neutral buffered formalin. The fixed tissue samples were then acid decalcified (using Easy-cut TM reagent, American Histology Reagent Co., Modesto, Calif.), and serial sections were processed by routine histologic methods using hematoxylin and eosin to stain the 4-μm sections.

The decalcified stained sections were evaluated for general characteristics and quality of healing. In addition, representative longitudinal sections taken from the center of the defect were examined using a BioQuant IV TM computer image analysis system. Selected indices of bone formation and resorption were measured including TBV, % OS, % OV, OW, % Ob/Ost, % Ob/TS, TRS, and #Oc/SL. Sections from all animals were analyzed histomorphometrically using a random stratified sampling scheme that systematically evaluated selected fields from the bony edge of the defect and the entire area within the defect. Fields were selected using a grid pattern, such that each field within the defect area had an equal probability of being selected. Approximately equal numbers of fields were evaluated for both the control and treated defects.

Statistical analysis

Statistical analysis was done as described above. Each group contained 3 to 4 rabbits.

Results

Preliminary results from radiographs indicate that the defect filled more rapidly in rabbits administered TGF-β1 formulated with TCP plus amylopectin than the untreated control or the groups with TCP plus amylopectin alone. The defects administered TGF-β1 tended to be filled with radiodense material by 21 days, while defects administered TCP plus amylopectin alone were less dense radiographically at 21 or 28 days. Defects that were untreated exhibited minimal filling within the 28-day observation period. Histologic data is expected to confirm the radiographic data, in that the TGF-β1/TCP/amylopectin formulation is expected to increase most if not all histomorphometric parameters examined to a greater extent than the other two control formulations.

The result of wetting the TCP with the TGF-β first before adding amylopectin rather than adding the TGF-β to the mixture of TCP and amylopectin was a better pharmacological effect. Without being limited to any one theory, it is believed that the better efficacy of the preparation wherein TGF-β is first adsorbed onto TCP is due to the ability of the osteoblasts to form around the TCP particles where the TGF-β was localized.

These data further indicate that TCP/amylopectin will function as a carrier for TGF-β and provide a matrix on which bone can readily form across osseous defects. The TCP/amylopectin formulation is preferred in that it does not melt as rapidly as those with gelatin and could evenly disperse the large TCP granules yet be malleable and formable to regular defects like a putty.

EXAMPLE 10

The purpose of this study was to formulate the TGF-β in collagen and TCP.

Collagen CN (Prodex, Inc., Princeton, N.J.) was sterilized by ethylene oxide. The matrix was prepared by mixing an appropriate aliquot of rhTGF-β1 solution prepared as described in Example 4 with TCP ($\geq 5$ μm) and collagen aseptically using plate and spatula. The proportion of TCP:collagen:water was 6:1:6 (weight:weight:volume). The volume of water needed was replaced by the sterile TGF-β1 solution. The final dose that can be administered for the rabbit skull defect model is about 8-10 μg of TGF-β1, depending on the defect size. The amount of TCP powder in each studied animal can be about 500-750 mg.

The radiographic data indicated that the formulation of collagen+TCP+10 μg TGF-β was significantly ($p < 0.05$) more efficacious than collagen alone in the rabbit skull defect model described above.

What is claimed is:

1. A bone-inducing formulation consisting essentially of about 0.5 μg to about 5 mg of transforming growth factor-β and about 140 mg to about 50 g of tricalcium phosphate.

2. The formulation of claim 1 wherein the tricalcium phosphate is particles.

3. The formulation of claim 2 wherein the particles are granules or a powder.

4. The formulation of claim 3 wherein the transforming growth factor-β is adsorbed on the granules or powder.

5. The formulation of claim 3 wherein the tricalcium phosphate is in the form of granules with a diameter of about 120 to 500 μm.

6. The formulation of claim 1 further comprising a polymer selected from amylopectin, gelatin, collagen, agarose, or a mixture of these polymers, in an amount effective to enhance consistency of the formulation.

7. The formulation of claim 6 wherein the polymer is lyophilized before use.

8. A bone-inducing formulation consisting essentially of about 0.5 μg to about 5 mg transforming growth factor-β adsorbed onto about 140 mg to about 50 g of tricalcium phosphate particles.

9. The formulation of claim 8 wherein about 1 μg to about 3 mg transforming growth factor-β is adsorbed onto the tricalcium phosphate particles.

10. The formulation of claim 8 wherein the size of the particles is about 120–500 μm.

11. The formulation of claim 10 wherein the size of the particles is about 125–250 μm.

12. A bone-inducing formulation consisting essentially of about 0.5 μg to about 5 mg transforming growth factor-β, about 140 mg to about 50 g tricalcium phosphate particles, and an amount of amylopectin that ranges from about 0.1:1 to 1:1 amylopectin:tricalcium phosphate.

13. The formulation of claim 12 wherein the amount of amylopectin ranges from about 0.25:1 to 0.5:1 amylopectin:tricalcium phosphate.

14. The formulation of claim 12 wherein the size of the particles is no less than about 75 μm and the ratio of tricalcium phosphate:amylopectin:TGF-β solution is about 1:0.5:0.5.

15. The formulation of claim 12 wherein the size of the particles is about 120–500 μm.

16. A method of producing a bone-inducing formulation of transforming growth factor-β consisting essentially of admixing an effective amount of a liquid solution of the transforming growth factor-β with tricalcium phosphate granules for a sufficient period of time to adsorb the transforming growth factor-β onto the granules and contacting the resulting mixture with an effective amount of amylopectin.

17. The method of claim 16 wherein the size of the granules is about 120 to 500 μm.

* * * * *

UNITED STATES PATENT AND TRADEMARK OFFICE
CERTIFICATE OF CORRECTION

PATENT NO.      : 5,422,340                                                Page 1 of 1
DATED           : June 6, 1995
INVENTOR(S)     : Ammann et al.

It is certified that error appears in the above-identified patent and that said Letters Patent is hereby corrected as shown below:

<u>Title page,</u>
Item [60], Related U.S. Application Data, the paragraph should read,
-- Continuation of Ser. No. 08/003,365, Jan. 12, 1993, abandoned, which is a continuation-in-part of Ser. No. 07/790,856, Nov. 12, 1991, abandoned, which is a divisional of Ser. No. 07/401,906, Sept. 1, 1989, Pat. No. 5,158,934. --

Signed and Sealed this

Twenty-second Day of July, 2003

JAMES E. ROGAN
*Director of the United States Patent and Trademark Office*